US011551783B2

(12) United States Patent
Nakagawa et al.

(10) Patent No.: US 11,551,783 B2
(45) Date of Patent: Jan. 10, 2023

(54) LABEL SELECTION SUPPORT SYSTEM, LABEL SELECTION SUPPORT DEVICE, METHOD OF SUPPORTING LABEL SELECTION, AND PROGRAM FOR SUPPORTING LABEL SELECTION

(71) Applicant: Sony Corporation, Tokyo (JP)

(72) Inventors: Kazuhiro Nakagawa, Saitama (JP); Teruaki Iyama, Kanagawa (JP); Takuya Kishimoto, Tokyo (JP)

(73) Assignee: Sony Corporation, Tokyo (JP)

( * ) Notice: Subject to any disclaimer, the term of this patent is extended or adjusted under 35 U.S.C. 154(b) by 226 days.

(21) Appl. No.: 16/479,725

(22) PCT Filed: Oct. 12, 2018

(86) PCT No.: PCT/JP2018/038024
§ 371 (c)(1),
(2) Date: Jul. 22, 2019

(87) PCT Pub. No.: WO2019/106973
PCT Pub. Date: Jun. 6, 2019

(65) Prior Publication Data
US 2021/0335450 A1  Oct. 28, 2021

(30) Foreign Application Priority Data

Nov. 29, 2017  (JP) .............................. JP2017-228662

(51) Int. Cl.
*G16B 25/10* (2019.01)
*G06N 20/00* (2019.01)
(Continued)

(52) U.S. Cl.
CPC ............. *G16B 25/10* (2019.02); *G06N 20/00* (2019.01); *G16B 40/00* (2019.02); *G16B 45/00* (2019.02)

(58) Field of Classification Search
USPC .......................................................... 702/19
See application file for complete search history.

(56) References Cited

U.S. PATENT DOCUMENTS

2013/0260379 A1  10/2013  Alexander et al.
2016/0025621 A1   1/2016  Kapinsky
(Continued)

FOREIGN PATENT DOCUMENTS

EP       3382393 A1    10/2018
JP    2003-083894 A     3/2003
(Continued)

OTHER PUBLICATIONS

International Search Report and English translation thereof dated Jan. 8, 2019 in connection with International Application No. PCT/JP2018/038024.
(Continued)

*Primary Examiner* — Pierre E Elisca
(74) *Attorney, Agent, or Firm* — Wolf, Greenfield & Sacks, P.C.

(57) ABSTRACT

There is provided a technology that supports selection of a label to be used for analysis of target molecules. The present technology provides a label selection support system including an information acquisition unit that obtains, via a network, information associated with a plurality of target molecules to be analyzed, an information processor that obtains, using the information associated with a plurality of target molecules, in vivo expression information of the plurality of target molecules from a database storing in vivo expression information of target molecules and generates support information associated with assignment of a label to each of the plurality of target molecules on the basis of the expression information, and a transmitter that transmits the generated support information via the network.

22 Claims, 9 Drawing Sheets

(51) Int. Cl.
 *G16B 40/00* (2019.01)
 *G16B 45/00* (2019.01)

(56) References Cited

U.S. PATENT DOCUMENTS

| | | |
|---|---|---|
| 2018/0231452 A1 | 8/2018 | Ren et al. |
| 2022/0073987 A1* | 3/2022 | Freije ................ B01L 3/502761 |

FOREIGN PATENT DOCUMENTS

| | | |
|---|---|---|
| JP | 2014-206551 A | 10/2014 |
| JP | 2016517000 A | 6/2016 |
| WO | WO 2014-144826 A1 | 9/2014 |
| WO | WO 2017-011549 A1 | 1/2017 |

OTHER PUBLICATIONS

Mizushima N., Correct knowledge prevents fabrication: 6 points to interpret data appropriately, Protein Nucleic Acid and Enzyme, 2009;54(2):185-194.

International Written Opinion and English translation thereof dated Jan. 8, 2019 in connection with International Application No. PCT/JP2018/038024.

Extended European Search Report dated Feb. 26, 2020 in connection with European Application No. 18884363.5.

International Preliminary Report on Patentability and English translation thereof dated Jun. 11, 2020 in connection with International Application No. PCT/JP2018/038024.

No Author Listed, Flow cytometry panel design: The basics. Multiplex flow cytometry experiments need the right combination of fluorophores. Molecular Probes™ Journal of Cell Biology Applications. Jun. 1, 2015, v71 pp. 20-22.

Dinkla et al., Screenit: Visual Analysis of Cellular Screens. IEEE transactions on visualization and computer graphics. Jan. 2017; v 23(1):591.

Mizushima N., Correct knowledge prevents fabrication: 6 points to interpret data appropriately, Protein Nucleic Acid and Enzyme, Feb. 1, 2009;54(2):185-194.

Nobutaka Kiyokawa, other 9person,Immunocytological diagnosis of pediatric leukemia using 9-color flow cytometry,a cytometry research [online], and 20 volumes, No. 2, Jun. 12, 2017, p. 27-33, date of search: Oct. 19, 2022, DOI: https://doi.org/10. 18947/cytometryresearch.20.2_27.

* cited by examiner

FIG. 3
A
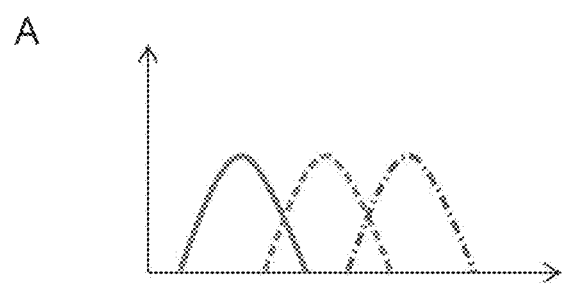
B
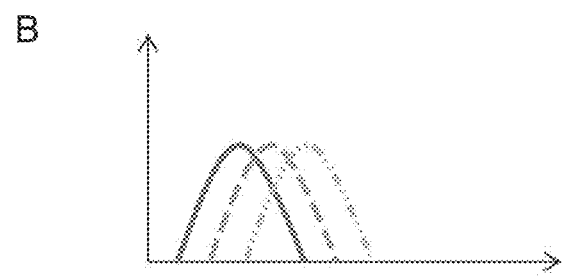
C
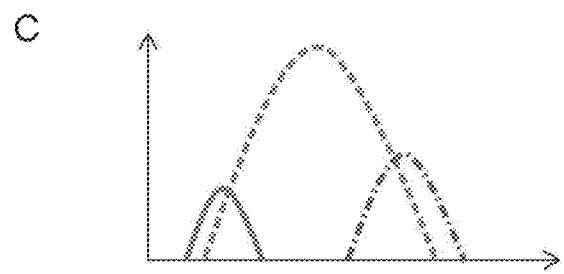

FIG. 4

Molecule 1

A

| Cell A | Cell B | Cell C | Cell D | Cell E | Cell F |
|---|---|---|---|---|---|
| 1.E+02 | 5.E+01 | 1.E+01 | 0.E+00 | 0.E+00 | 0.E+00 |

B

| | |
|---|---|
| Plasma membrane | 5 |
| ER | 3 |
| Golgi | 2 |
| Mitochondria | 1 |
| Lysosome | 1 |
| Nucleus | 0 |
| Cytosol | 0 |
| Extracellular | 2 |

C

| | Cell A | Cell B | Cell C | Cell D | Cell E | Cell F |
|---|---|---|---|---|---|---|
| Plasma membrane | 5.E+02 | 3.E+02 | 5.E+01 | 0.E+00 | 0.E+00 | 0.E+00 |
| ER | 3.E+02 | 2.E+02 | 3.E+01 | 0.E+00 | 0.E+00 | 0.E+00 |
| Golgi | 2.E+02 | 1.E+02 | 2.E+01 | 0.E+00 | 0.E+00 | 0.E+00 |
| Mitochondria | 1.E+02 | 5.E+01 | 1.E+01 | 0.E+00 | 0.E+00 | 0.E+00 |
| Lysosome | 1.E+02 | 5.E+01 | 1.E+01 | 0.E+00 | 0.E+00 | 0.E+00 |
| Nucleus | 0.E+00 | 0.E+00 | 0.E+00 | 0.E+00 | 0.E+00 | 0.E+00 |
| Cytosol | 0.E+00 | 0.E+00 | 0.E+00 | 0.E+00 | 0.E+00 | 0.E+00 |
| Extracellular | 2.E+02 | 1.E+02 | 2.E+01 | 0.E+00 | 0.E+00 | 0.E+00 |

FIG. 5

Molecule 2

A

| Cell A | Cell B | Cell C | Cell D | Cell E | Cell F |
|---|---|---|---|---|---|
| 2.E+02 | 5.E+02 | 3.E+01 | 5.E+01 | 0.E+00 | 0.E+00 |

B

| | |
|---|---|
| Plasma membrane | 5 |
| ER | 3 |
| Golgi | 2 |
| Mitochondria | 1 |
| Lysosome | 1 |
| Nucleus | 0 |
| Cytosol | 0 |
| Extracellular | 2 |

C

| | Cell A | Cell B | Cell C | Cell D | Cell E | Cell F |
|---|---|---|---|---|---|---|
| Plasma membrane | 1.E+03 | 3.E+03 | 2.E+02 | 3.E+02 | 0.E+00 | 0.E+00 |
| ER | 6.E+02 | 2.E+03 | 9.E+01 | 2.E+02 | 0.E+00 | 0.E+00 |
| Golgi | 4.E+02 | 1.E+03 | 6.E+01 | 1.E+02 | 0.E+00 | 0.E+00 |
| Mitochondria | 2.E+02 | 5.E+02 | 3.E+01 | 5.E+01 | 0.E+00 | 0.E+00 |
| Lysosome | 2.E+02 | 5.E+02 | 3.E+01 | 5.E+01 | 0.E+00 | 0.E+00 |
| Nucleus | 0.E+00 | 0.E+00 | 0.E+00 | 0.E+00 | 0.E+00 | 0.E+00 |
| Cytosol | 0.E+00 | 0.E+00 | 0.E+00 | 0.E+00 | 0.E+00 | 0.E+00 |
| Extracellular | 4.E+02 | 1.E+03 | 6.E+01 | 1.E+02 | 0.E+00 | 0.E+00 |

*FIG. 6*
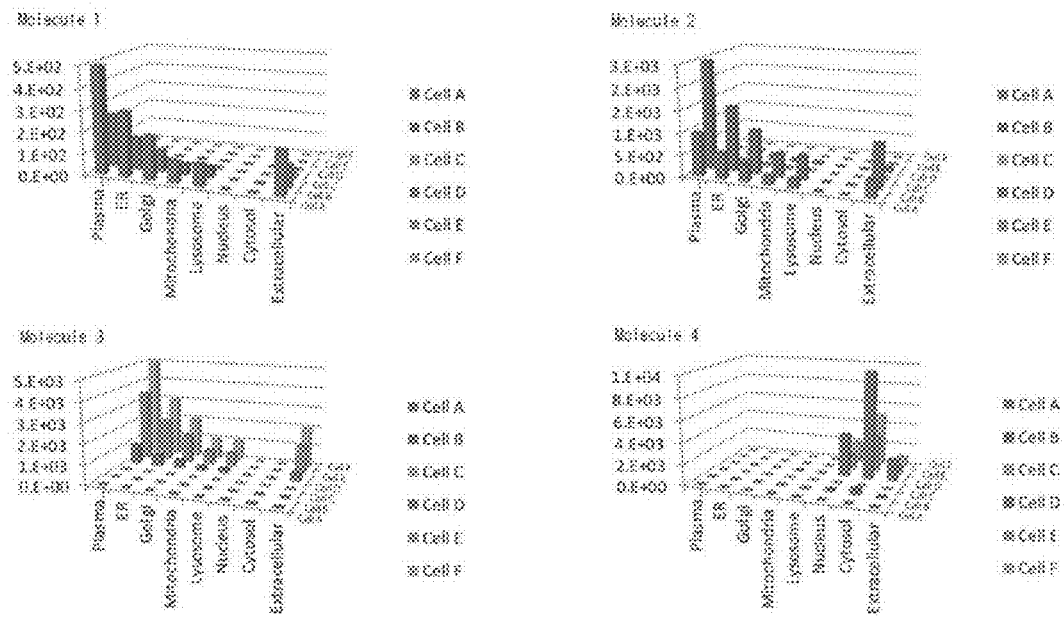
*FIG. 7*
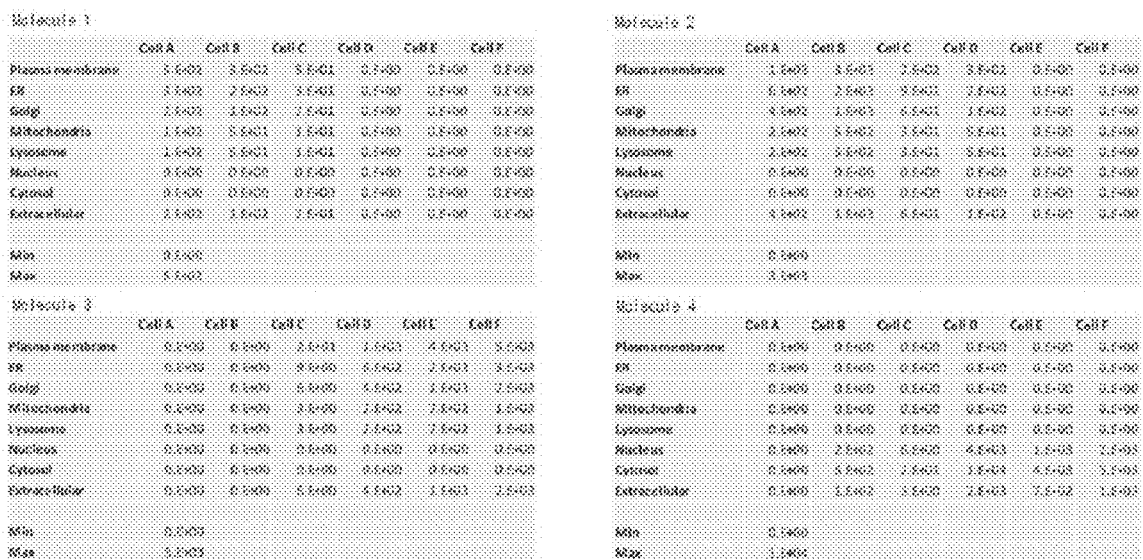
*FIG. 8*
|  | Molecule 1 | Molecule 2 | Molecule 3 | Molecule 4 |
|---|---|---|---|---|
| Molecule 1 | 1 | 0.6851 | -0.2555 | -0.1741 |
| Molecule 2 | 0.6851 | 1 | -0.24 | -0.1699 |
| Molecule 3 | -0.2555 | -0.24 | 1 | -0.1498 |
| Molecule 4 | -0.1741 | -0.1699 | -0.1498 | 1 |

LABEL SELECTION SUPPORT SYSTEM, LABEL SELECTION SUPPORT DEVICE, METHOD OF SUPPORTING LABEL SELECTION, AND PROGRAM FOR SUPPORTING LABEL SELECTION

CROSS-REFERENCE TO RELATED APPLICATIONS

This is a U.S. National Stage Application under 35 U.S.C. § 371, based on International Application No. PCT/JP2018/038024, filed in the Japanese Patent Office as a Receiving Office on Oct. 12, 2018, entitled "LABEL SELECTION SUPPORT SYSTEM, LABEL SELECTION SUPPORT DEVICE, METHOD OF SUPPORTING LABEL SELECTION, AND PROGRAM FOR SUPPORTING LABEL SELECTION", which claims priority under 35 U.S.C. § 119(a)-(d) or 35 U.S.C. § 365(b) to Japanese Patent Application Number JP2017-228662, filed in the Japanese Patent Office on Nov. 29, 2017, each of which applications is hereby incorporated by reference in its entirety.

TECHNICAL FIELD

The present technology relates to a label selection support system, a label selection support device, a method of supporting label selection, and a program for supporting label selection. More particularly, the present technology relates to a label selection support system, a label selection support device, a method of supporting label selection, and a program for supporting label selection used to provide support information associated with assignment of a label suitable for analysis of a plurality of target molecules.

BACKGROUND ART

Various kinds of analysis using labels have been carried out to analyze target molecules. For example, detection and/or analysis of target molecules, such as antigenic proteins, using an antibody labeled with a plurality of fluorescent dyes has been carried out with a flow cytometer or a microscope. Furthermore, in addition to antigen-antibody reaction, detection and analysis of target molecules by nucleic acid hybridization using a fluorescently labeled nucleic acid probe, and detection and analysis of enzyme molecules using a fluorescently labeled substrate have been widely carried out. Various fluorescent dyes have been used in those detections and/or analyses. Each fluorescent dye has a unique characteristic, such as a unique fluorescent spectrum and fluorescent intensity.

For example, Patent Document 1 set out below discloses an invention related to a technology for analyzing a type of fluorescence emitted from microparticles and the like (par. 0001). Patent Document 1 set out below discloses "a method of displaying data regarding fluorescent spectrum obtained in such a manner that detected data, which is obtained by simultaneously detecting fluorescence emitted from microparticles flowing through a flow channel in a plurality of wavelength regions, is integrated or averaged with respect to a plurality of microparticles" (claim 1).

CITATION LIST

Patent Document

Patent Document 1: Japanese Patent Application Laid-Open No. 2014-206551

SUMMARY OF THE INVENTION

Problems to be Solved by the Invention

It is necessary to select a fluorescent dye for detecting and/or analyzing a target molecule to perform, for example, the above-described detection and/or analysis on the target molecule. Furthermore, it may also be necessary to adjust fluorescent intensity of the fluorescent dye to be used. While selection of the fluorescent dye is generally performed by a user who carries out detection and/or analysis of the target molecule, it is a time-consuming task even if the user is experienced. Furthermore, a selected fluorescent dye may not be suitable for the detection and/or analysis of the target molecule.

In view of the above, it is an object of the present technology to provide a technology for supporting selection of labels used for detection and/or analysis of target molecules.

Solutions to Problems

The present inventors have found that the problems described above can be solved by a system having a specific configuration.

That is, the present technology provides a label selection support system including:

an information acquisition unit that obtains, via a network, information associated with a plurality of target molecules to be analyzed;

an information processor that obtains, by using the information associated with the plurality of target molecules, in vivo expression information of the plurality of target molecules from a database storing in vivo expression information of target molecules, and generates support information associated with assignment of a label to each of the plurality of target molecules on the basis of the expression information; and a transmitter that transmits the generated support information via the network.

According to one mode of the present technology, the expression information can be information associated with in vivo expression distribution or an in vivo expression level.

According to one mode of the present technology, the expression information is information associated with an in vivo expression level, and the information processor can select fluorescent intensity of a label to be assigned to the target molecules on the basis of the information associated with the expression level of the target molecules.

According to one mode of the present technology, the expression information is information associated with in vivo expression distribution, and the information processor can select a fluorescence wavelength of a label to be assigned to the target molecules on the basis of the information associated with the expression distribution of the target molecules.

According to one mode of the present technology, the information processor can assign a fluorescent dye far in fluorescence wavelength spectrum to each of the plurality of target molecules spatially adjacent to each other.

According to one mode of the present technology, the information processor can use a learned model in which suitability of a combination of a target molecule and a label has been learned to generate the support information.

According to one mode of the present technology, the information processor can include a data table generator that generates a data table for each of the target molecules from the expression information.

According to one mode of the present technology, the information processor can further include a support information generator that refers to the generated data table and generates support information associated with a label to be assigned to each of the target molecules.

According to one mode of the present technology, the support information generator can generate the support information on the basis of a correlation between the generated data tables.

According to one mode of the present technology, the label can be a dye.

According to one mode of the present technology, the label can be a fluorescent dye, and the support information generator can assign a label to each of the target molecules in such a manner that, on the basis of a correlation between the generated data tables, a fluorescent dye farther in wavelength is assigned to each of two target molecules having a stronger correlation between the data tables.

According to one mode of the present technology, the data table generator can further include a data table generation rule determiner that determines a generation rule of the data table using a classifier generated on the basis of information associated with target molecules and information associated with analysis of the target molecules.

According to one mode of the present technology, the support information generator can further include a support information generation rule determiner that determines a generation rule of the support information using a classifier generated on the basis of information associated with target molecules and information associated with analysis of the target molecules.

According to one mode of the present technology, the target molecule can be a biomolecule.

According to one mode of the present technology, the data table generator can generate, for each of the target molecules, a data table having data related to an amount of the target molecules in a cell.

According to one mode of the present technology, the information processor can further obtain, in addition to the expression information, data related to a treatment condition before analysis of a biomolecule.

According to one mode of the present technology, the data table generator can generate, for each biomolecule, a treatment condition data table including a treatment condition before analysis of the biomolecule as an item.

According to one mode of the present technology, the information processor may further include a treatment condition selection unit that refers to the treatment condition data table generated for each biomolecule to select a treatment condition under which more biomolecules can be analyzed.

According to one mode of the present technology, the information processor can be further configured to: obtain device information associated with a device for analyzing the target molecules; obtain, from a database, label data that can be used in the device on the basis of the device information; and then select a label to be assigned to the target molecules from labels included in the label data.

Furthermore, the present technology also provides a label selection support device including an information processor that obtains, by using information associated with a plurality of target molecules to be analyzed, in vivo expression information of the plurality of target molecules from a database storing in vivo expression information of target molecules, and generates support information associated with assignment of a label to each of the plurality of target molecules on the basis of the expression information.

Furthermore, the present technology also provides a method of supporting label selection, including:

an expression information obtaining step of, by using information associated with a plurality of target molecules to be analyzed, obtaining in vivo expression information of the plurality of target molecules from a database storing in vivo expression information of the target molecules; and a support information generating step of generating support information associated with assignment of a label to each of the plurality of target molecules on the basis of the expression information.

Furthermore, the present technology also provides a program for supporting label selection, causing a computer to execute:

an expression information obtaining step of, by using information associated with a plurality of target molecules to be analyzed, obtaining in vivo expression information of the plurality of target molecules from a database storing in vivo expression information of the target molecules; and a support information generating step of generating support information associated with assignment of a label to each of the plurality of target molecules on the basis of the expression information.

Effects of the Invention

According to the present technology, it is possible to provide information that contributes to selection of labels used for detection and/or analysis of target molecules. According to the present technology, even a relatively inexperienced user can select a label more easily. Note that the effects exerted by the present technology are not necessarily limited to the effects described herein, and may be any of the effects described in the present specification.

BRIEF DESCRIPTION OF DRAWINGS

FIG. 3 is a graph illustrating exemplary fluorescent intensity and wavelengths of three fluorescent dyes.

FIG. 4 is a data table illustrating expression levels in various regions in various cell types.

FIG. 5 is another data table illustrating expression levels in various regions in various cell types.

FIG. 6 is a three-dimensional matrix diagram of expression levels.

FIG. 7 is another data table illustrating expression levels in various regions in various cell types.

FIG. 8 is a table illustrating correlation coefficients between molecules.

MODE FOR CARRYING OUT THE INVENTION

Figure 1:
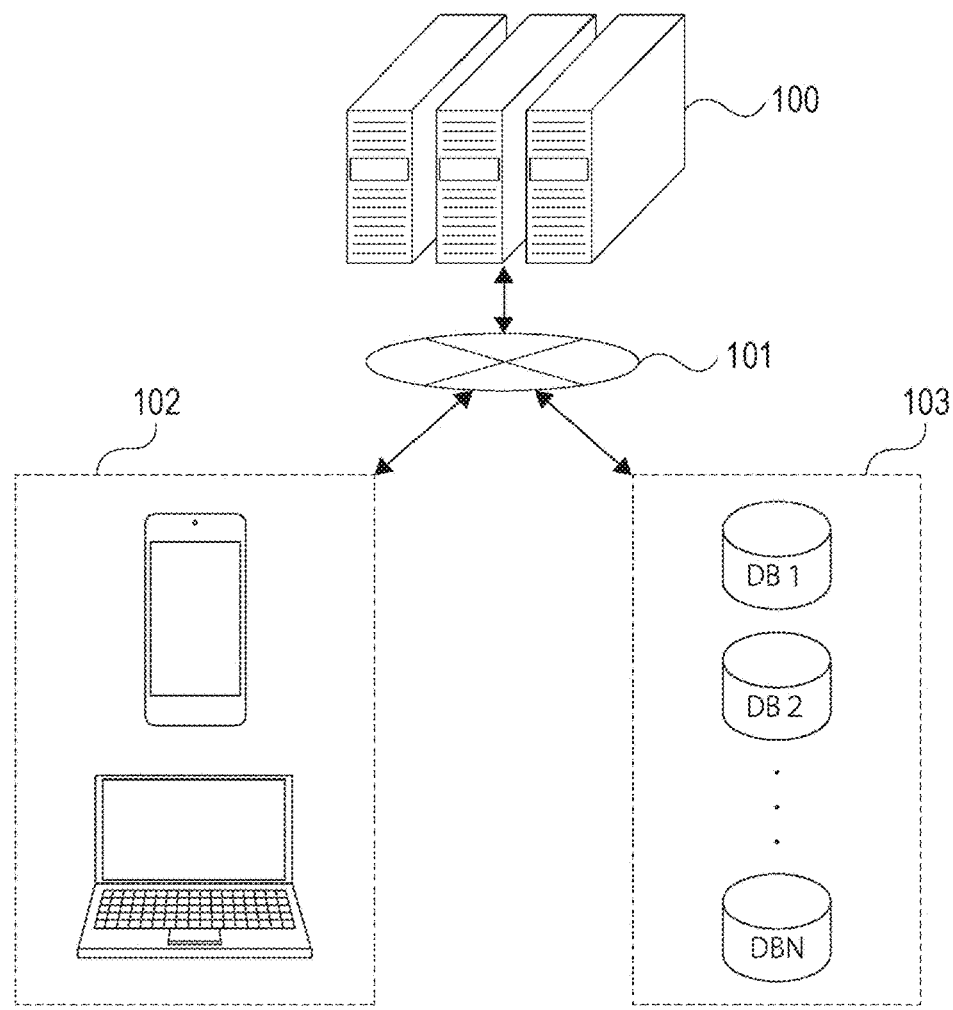
FIG. 1 is a schematic diagram illustrating an exemplary situation in which a label selection support system according to the present technology is used.

Hereinafter, preferred embodiments for implementing the present technology will be described. Note that the embodiments to be described below show representative embodiments of the present technology, and the scope of the present technology is not limited to those described herein. Note that descriptions will be given in the following order.

1. Main Problems and Basic Concept of the Present Technology
2. First Embodiment (Label Selection Support System)
   (1) Description of First Embodiment
   (2) First Example of First Embodiment (Label Selection Support System)
   (3) Second Example of First Embodiment (Label Selection Support System)
   (4) Third Example of First Embodiment (Label Selection Support System)
3. Second Embodiment (Label Selection Support Device)
   (1) Description of Second Embodiment
   (2) Example of Second Embodiment (Label Selection Support Device)
4. Third Embodiment (Method of Supporting Label Selection)
   (1) Description of Third Embodiment
   (2) First Example of Third Embodiment (Method of Supporting Label Selection)
5. Fourth Embodiment (Program for Supporting Label Selection)
   (1) Description of Fourth Embodiment
   (2) Example of Fourth Embodiment (Program for Supporting Label Selection)
6. Exemplary Hardware Configuration 1. Main Problems and Basic Concept of the Present Technology First, an exemplary task in analysis using a fluorescent dye will be described with reference to FIG. 3.

FIG. 3 illustrates exemplary fluorescent intensity and wavelengths of three fluorescent dyes. In any of the graphs illustrated in FIG. 3, a vertical axis represents fluorescent intensity, and a horizontal axis represents a wavelength. As illustrated in FIG. 3A, in a case where the wavelengths of the three fluorescent dyes are separated, it is easy to perform color separation in analysis using those fluorescent dyes. Furthermore, in a case where fluorescent intensity of respective fluorescent dyes is uniform as illustrated in FIG. 3A, it is easy to perform color separation.

FIGS. 3B and 3C illustrate other examples of the fluorescent intensity and the wavelengths of the three fluorescent dyes. As illustrated in FIG. 3B, in a case where spectra of the three fluorescent dyes largely overlap with each other, it may be difficult to perform color separation in analysis using those fluorescent dyes. Furthermore, as illustrated in FIG. 3C, if the wavelengths of those three fluorescent dyes are separated, the overlap of measured wavelengths becomes large in analysis using those fluorescent dyes in a case where fluorescent intensity of a certain fluorescent dye is significantly large compared with others, whereby it may be difficult to perform color separation.

As described above with reference to FIG. 3, in a case where a plurality of fluorescent dyes is used in analysis, the fluorescent dyes to be used need to be carefully selected in consideration of the characteristic of each fluorescent dye. Selection of the fluorescent dyes can be difficult for even experienced users, and thus can be even more difficult for less experienced users. Such difficulty is more pronounced especially in a case where a large number of fluorescent dyes is used in one analysis.

Furthermore, since various kinds of fluorescent dyes are commercially available these days, it is required to select a fluorescent dye more suitable for analysis even in a case where one fluorescent dye is selected.

Furthermore, in the analysis using a fluorescent dye, it is frequently necessary to consider not only a review of the fluorescent dye to be used but also the performance of the device itself used for the analysis and the setting of a fluorescence detector of the device.

As described above, it is commonly difficult to select a fluorescent dye. In view of the above, there has been a need for technology that makes it possible to select a fluorescent dye more easily.

Note that, although there is software that proposes a combination of dyes that can be selected from wavelength spectrum information of the dyes, there is still a need to make adjustments on the basis of experience of the user, whereby technology that can make a better proposal is required.

In the present technology, in vivo expression information of a plurality of target molecules is obtained from, using information associated with the plurality of target molecules, a database storing in vivo expression information of target molecules, and support information associated with assignment of a label to each of the plurality of target molecules is generated on the basis of the expression information. As a result, it becomes possible to propose, to the user, a label suitable for analysis of a plurality of target molecules. For example, data regarding a position where a target molecule exists, such as an expression region, an amount of the target molecules, such as an expression level, an analytical condition of the target molecule, such as an activation condition (particularly, antigenic activation condition in antigen-antibody reaction), and/or information associated with an analyzer, such as a wavelength range of a fluorescent dye that can be used, and the like can be obtained from the database. By referring to a data table created from such data, it becomes possible to propose, to the user, support information associated with a label suitable for analysis of the target molecule.

In the present technology, for example, an existing protein expression database, a genetic expression database, an article database, and/or a microarray experiment database can be used as a database storing expression information, for example. That is, in the present technology, a proposal regarding assignment of a label to be used for analysis can be made on the basis of existing data. Therefore, according to the present technology, even a relatively inexperienced user can select a label more easily without examining existing data. Furthermore, a proposal regarding assignment of a label based on existing data is made according to the present technology, whereby the number of trial and error can be reduced.

2. First Embodiment (Label Selection Support System)

(1) Description of First Embodiment

The present technology provides a label selection support system including an information acquisition unit that obtains, via a network, information associated with a plurality of target molecules to be analyzed, an information processor that obtains, using the information associated with a plurality of target molecules, in vivo expression information of the plurality of target molecules from a database storing in vivo expression information of target molecules and generates support information associated with assignment of a label to each of the plurality of target molecules on the basis of the expression information, and a transmitter that transmits the generated support information via the network.

The label selection support system according to the present technology may be a system in which the information acquisition unit, the information processor, and the transmitter are incorporated in one device, or may be a system in which those components are distributed to a plurality of devices to exert any of effects of the present technology.

According to one mode of the present technology, the information processor can include a data table generator that generates a data table for each of the target molecules from the expression information. In the present technology, support information can be generated on the basis of the data table.

According to one mode of the present technology, the information processor can include a support information generator that refers to the generated data table and generates support information associated with a label to be assigned to each of the target molecules.

The support information generator refers to the data table generated as described above, and generates support information associated with assignment of a label to each of the target molecules. By referring to the support information, a user who analyzes the target molecules can easily select a label suitable for the analysis of each target molecule.

In the present technology, the target molecules indicate molecules that can be made possible to be analyzed by labels, which may be appropriately selected by those skilled in the art. For example, the target molecules can be molecules that can be made possible to be analyzed by labels in analysis such as flow cytometry, microscopy, Western blot, various arrays, and ELISA. In other words, the present technology can be used to assist in selection of labels used in those analyses.

In the present technology, the target molecules particularly indicate molecules that can be present in vivo, examples of which include biomolecules, drug molecules, and toxic molecules, and more particularly, it can be biomolecules. Examples of the biomolecules include nucleic acids, proteins, saccharides, lipids, and vitamins. Examples of the nucleic acids include DNA and RNA. Examples of the proteins include antigenic proteins, such as cell surface markers, antibodies, enzyme proteins, structural proteins, and adhesive proteins.

In the present technology, the number of the target molecules to be analyzed may be plural, which is, for example, 2 or more, more preferably, 3 or more, 5 or more, 10 or more, 15 or more, or 20 or more. As the number of the target molecules increases, selection of labels tends to be more difficult for the user, whereby the effect of making the selection of labels easier is more pronounced.

In the present technology, the information associated with target molecules can be information for identifying a target molecule. Examples of such information include, but are not limited to, a name or an abbreviation of a target molecule, and a number or a code for indicating a target molecule.

In the present technology, a label can be a substance used to analyze a target molecule. In the present technology, labels known in the art may be used. The label is, for example, a dye, particularly a fluorescent dye. In the present technology, the dye may be, for example, a compound that directly binds to a target molecule, or may be a compound used in the state of being bound to an antibody (e.g., IgG, etc.). For example, various kinds of fluorescent dyes having a fluorescence wavelength in the visible light region can be used as a dye. Examples of labels include, but are not limited to, fluorescent dyes of AlexaFluor (registered trademark) series, fluorescent dyes of DyLight (registered trademark) series, and fluorescent dyes of BD Horizon Brilliant (registered trademark) series. In the present technology, the dye may be one expressed as a part of a target molecule, which is, for example, a fluorescent protein contained in a fluorescent fusion protein or the like. Examples of the fluorescent protein include GFP, BFP, CFP, EGFP, EYFP, and PA-GFP.

In the present technology, the label also includes an antibody to which a fluorescent dye is bound. A method of analyzing a target molecule using an antibody to which a fluorescent dye is bound is also referred to as fluorescent immunostaining. The fluorescent immunostaining can include, for example, immunocytochemistry (ICC), and immunohistochemistry (IHC). In ICC, staining of cells isolated from tissue or cultured cells may be performed. In IHC, target molecules in thin sections of tissue can be stained. In the present technology, support information for selecting a label to be used preferably in fluorescent immunostaining, in other words, an antibody to which a fluorescent dye is bound, can be generated.

The fluorescent immunostaining includes direct fluorescent immunostaining and indirect fluorescent immunostaining. In the former, an antibody to which a fluorescent dye is bound directly binds to a target molecule. Then, the fluorescent dye is detected, whereby analysis of the target molecule can be performed. In the latter, an antibody (also referred to as secondary antibody) to which a fluorescent dye is bound binds to an antibody (also referred to as primary antibody) specifically bound to a target molecule. In other words, the secondary antibody to which the fluorescent dye is bound binds to the target molecule via the primary antibody.

In the present technology, examples of the support information associated with assignment of a label include:
a name (e.g., compound name), an abbreviation (e.g., abbreviation of compound name), an item number, or a trade name of a label to be assigned to the target molecule;
a range of wavelengths that the label should have;

a list of one or a plurality of dyes having a fluorescence wavelength in the wavelength range that the label should have;

a range of fluorescent intensity that the label should have;
a chemical structure that the label should have; and
labels or wavelength ranges that should not be assigned to the target molecule.

In the present technology, the database may be, for example, a database published on the Internet, or may be a database not published on the Internet, such as a database owned by the user. In the present technology, one or a plurality of databases may be used. Examples of the database used in the present technology include, but are not limited to, a protein expression database, a genetic expression database, an article database, a microarray experiment database, and a database associated with labels. The database may be appropriately selected by those skilled in the art on the basis of the type of the target molecule, or may be automatically selected by the label selection support system according to the present technology on the basis of the type of the target molecule. The information processor identifies the type of the target molecule from the information associated with target molecules obtained by the information acquisition unit, and the information processor can select, on the basis of the type, the database associated with the molecule of the type. Accordingly, for example, in a case where the target molecule is RNA, a database associated with RNA is automatically selected. In a preferred mode of the present technology, the protein expression database can be used as a database.

Examples of the database used in the present technology include the followings. Any of them is a database published on the Internet. Among the followings, it is more preferable to use GeneCards and/or ProteomicsDB, which is a protein expression database.

GeneCards (trademark) (http://www.genecards.org/)
ProteomicsDB (https://www.proteomicsdb.org/proteomicsdb/#overview)
Gene Expression Omnibus (https://www.ncbi.nlm.nih.gov/geo/)
Gene eXpression Database (http://www.informatics.jax.org/expression.shtml)
Expression Atlas (https://www.ebi.ac.uk/gxa/home)
All Of gene Expression (http://aoe.dbcls.jp/)
Reference Expression dataset (http://refex.dbcls.jp/)

In the present technology, the expression information obtained by the information processor can be information associated with expression of the target molecule. Examples of the expression information include data related to an analysis result of the target molecule. Examples of the data related to an analysis result of the target molecule include, but are not limited to, data related to an amount of the target molecules (e.g., expression level, abundance, degree of expression, etc.), data related to a position, a region, a timing, or time at which the target molecule is present, and data related to a cell type or a species having the target molecule. The data related to a position or a region where the target molecule is present or a timing or time includes, for example, data related to a position, a region, a timing, or time at which the data related to an amount of the target molecules can be obtained. The data may be obtained as, for example, data related to an amount of the target molecules at a certain position, region, timing, or time. The position or the region can include, for example, an organ or a part, a position or a region in an organ or a part, and organelle.

In the present technology, the information processor can obtain, in addition to the expression information, data related to analytical conditions and/or data related to an analyzer.

Examples of the data related to analytical conditions include analytical conditions for obtaining the analysis result, such as treatment conditions before analysis, analytical conditions, and treatment conditions after analysis. The data related to analytical conditions include, for example, data related to analytical conditions in the case where the data related to an amount of the target molecules has been obtained. The data may be obtained as, for example, data related to an amount of the target molecules obtained in the case where analysis has been carried out under a certain analytical condition.

Examples of the data related to the analyzer include a name of the device, a type of the device, an operation condition of the device, a range of labels that can be used in the device, such as a wavelength range that can be analyzed by the device, and a range of reagents that can be used in the device.

For example, in a case where the target molecule is a biomolecule, examples of information obtained by the information processor include:

abundance or an expression level, expression distribution, a position or a region of existence or expression, and a degree of expression of the biomolecule;

a species, an age, and gender of organisms having biomolecules;

presence or absence of disease of the organisms having biomolecules, a type of the disease, and anamnesis;

a type, a source, and an obtaining method or a culture method of the organ or the cell expressing a biomolecule;

a timing of obtaining data (e.g., timing at which analytical data is published on the database); and the number of times the data is cited (e.g., the number of times articles disclosing the analytical data is cited).

One or two or more of those pieces of information may be obtained by the information processor.

According to one mode of the present technology, the expression information obtained by the information processor includes at least information associated with an amount of the target molecules, and more particularly, includes at least abundance or an expression level of the target molecule and/or a degree of expression of the target molecule.

The expression information obtained by the information processor can preferably be information associated with in vivo expression distribution or an expression level.

For example, the expression information obtained by the information processor is information associated with the in vivo expression level, and the information processor can select the fluorescent intensity of the label to be assigned to the target molecule on the basis of the information associated with the expression level of the target molecule.

For example, the expression information obtained by the information processor is information associated with the in vivo expression distribution, and the information processor can select the fluorescence wavelength of the label to be assigned to the target molecule on the basis of the information associated with the expression distribution of the target molecule.

According to another mode of the present technology, the expression information obtained by the information processor may include at least the information associated with an amount of the target molecules, and information associated with a position or a region where the target molecule is present.

According to still another mode of the present technology, the expression information obtained by the information processor may include at least the information associated with an amount of the target molecules, the information associated with a position or a region where the target molecule is present, and information associated with a species and/or a cell type having the target molecule.

Such expression information is used in the present technology, whereby support information that contributes to more appropriate assignment of labels is generated.

The use of appropriately assigned labels facilitates the analysis of target molecules.

For example, in a case where the intracellular distribution of a plurality of target molecules is different, color discrimination is easy even if the wavelengths of the used fluorescent dyes are close. This will be described with reference to FIG. 16.

Figure 16:
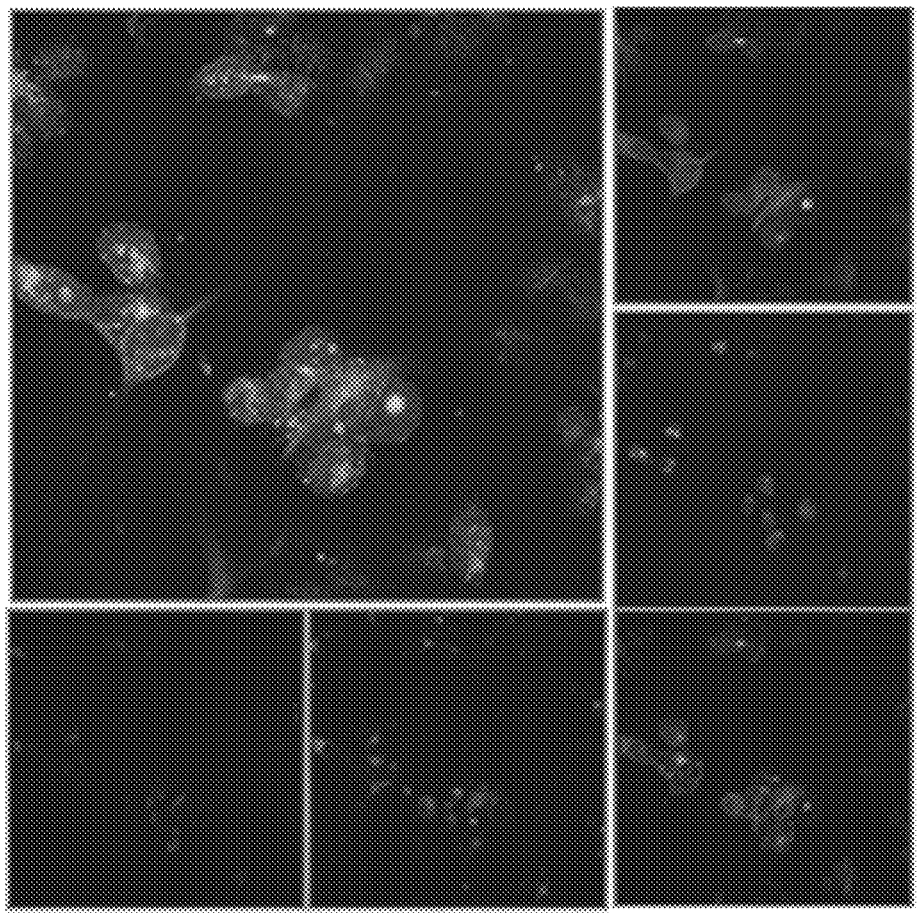
FIG. 16 is a photograph obtained by photographing, using a microscope, human mammary adenocarcinoma cells having been subject to fluorescent immunostaining.

FIG. 16 is a photograph obtained by photographing human mammary adenocarcinoma cells (MCF7) having been subject to fluorescent immunostaining using five dyes with a confocal laser scanning microscope (Olympus FV1000, ×60). In the fluorescent immunostaining, the fluorescent dye BV480 was used for a target molecule E-cadherin present on the cell surface, Alexa 488 was used for β-tubulin present in the cytoplasm, Alexa 555 was used for Ki-67 present in the nucleolus, Alexa 647 was used for GM130 present in the Golgi body, and BV421 was used for Lamp1 present in the lysosomal granulosa membrane.

As illustrated in FIG. 16, in a case where the intracellular distribution of the target molecules is different, color discrimination is easy.

Furthermore, in a case where cell distribution is different, color discrimination is easy even if the intracellular distribution of a plurality of target molecules is the same. This will be described with reference to FIG. 17.

Figure 17:
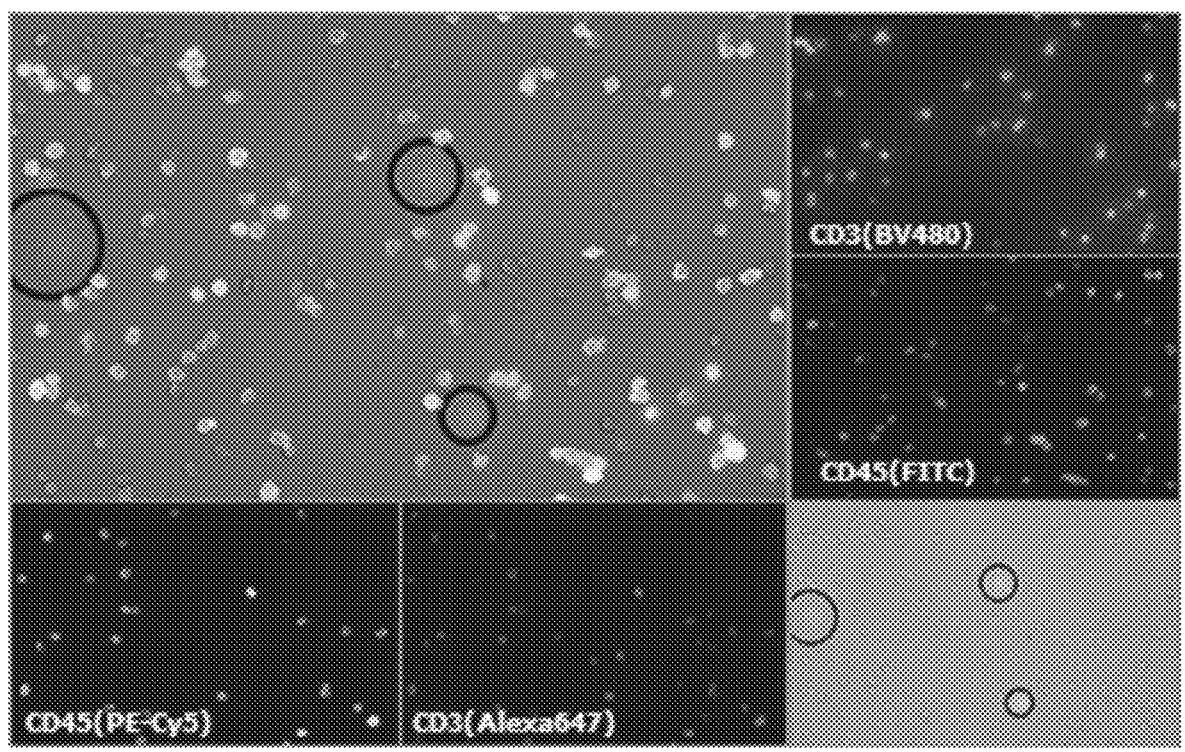
FIG. 17 is a photograph obtained by photographing, using a microscope, Jurkat cells having been subject to fluorescent immunostaining.

FIG. 17 is a photograph obtained by photographing, with a microscope, Jurkat cells having been subject to fluorescent immunostaining using four dyes. In the fluorescent immunostaining, the fluorescent dye BV480 (cyan) was used for the target molecule CD3, FITC (green) was used for CD45, Alexa 647 (red) was used for CD3, and PE-Cy5 (yellow) was used for CD45. Furthermore, the lower right photograph among the photographs in FIG. 17 is obtained by bright-field photographing. All target molecules are expressed on the cell surface.

As illustrated in FIG. 17, even in a case where all of the target molecules are expressed on the cell surface, color discrimination is easy if the cells expressing the target molecules are different.

According to one mode of the present technology, the data table can be generated from data obtained by the information processor for each target molecule. In order to generate the data table, for example, two, three, four, five, or more types of data can be used. According to one mode of the present technology, a two-dimensional data table can be generated from three types of data. Furthermore, according to another mode, a data table in which a two-dimensional data table is skewered, or a three-dimensional data table may be generated from four types of data. Alternatively, a two-dimensional data table can be generated using three types of data among four types of data, and data processing based on the remaining one type of data can be performed on the data of each cell of the data table. The data processing can be processing such as multiplication by a predetermined coefficient, for example.

According to a preferred mode of the present technology, the data table can have the data related to an amount of the target molecules (e.g., expression level, abundance, degree of expression, etc.) in each cell of the data table. For example, the data table can have the expression level in each cell of a table that includes, in the data table, two items (e.g., row item and column item) of the region where the target molecule is present and the cell type having the target molecule. In other words, the expression level of each cell represents the expression level of the target molecule in the region in the cell type. Note that the row item and the column item in the data table may be interchanged.

Other data may be used as the row item and the column item, and examples of the other data include, but are not limited to, pretreatment conditions, particularly types of treatment before analysis, and pH, a temperature, a reagent, a treatment period of time, and the like in the processing before the analysis.

Preferably, the information processor can respectively assign the fluorescent dye far in the fluorescence wavelength spectrum to a plurality of target molecules spatially adjacent to each other. A result of the assignment can be support information. For example, fluorescent dyes having farther fluorescence wavelength spectrum can be respectively assigned to two or more target molecules located closer in the cell. Accordingly, a combination of fluorescent dyes more suitable for analysis can be proposed to the user.

The information processor may use a learned model in which suitability of the combination of the target molecule and the label has been learned to generate the support information. One generated by a method known to those skilled in the art may be used as a learned model. The learned model may be, for example, a rule group to be described in the following "(4) Third Example of First Embodiment (Label Selection Support System)", or may be generated on the basis of the machine learning to be described in "(4) Third Example of First Embodiment (Label Selection Support System)".

According to one mode of the present technology, the support information associated with assignment of a label can be generated by the support information generator referring to the data table. According to one mode of the present technology, the support information can be generated on the basis of the correlation between data tables generated for each of the target molecules. For example, the support information generator obtains a correlation coefficient between data tables for two of the target molecules with respect to combinations (preferably all combinations) of the target molecules to be analyzed, and then generates the support information associated with assignment of a label on the basis of the obtained correlation coefficient.

According to one mode of the present technology, the support information generator can generate the support information associated with assignment of a label in accordance with a predetermined rule. For example, the support information generator can select one or a plurality of labels to be assigned to each target molecule in accordance with a predetermined rule, and then generate support information indicating that the selected label should be assigned to each target molecule. The rule may be stored in the support information generator in advance, or may be added by the user as necessary. Hereinafter, the rule will be described with examples.

(1-1) First Exemplary Rule

A first example of the assignment rule is the following Rule 1.

Rule 1: A fluorescent dye for each of the target molecules is selected in such a manner that a fluorescent dye having a farther wavelength is assigned to each of two target molecules having stronger correlation between data tables.

This rule can be applied especially to two target molecules having positive correlation between data tables. For example, for two target molecules having negative correlation, the support information generator may optionally assign a label other than the already assigned label, or the user may make a selection as appropriate. The fluorescent dyes are assigned to the target molecules in accordance with the rule, whereby spectral overlap is reduced and more appropriate labels can be assigned to the target molecules.

In a preferred mode, the rule can be applied in such a case where the element of the data table is the data related to an amount of the target molecules, and one of the items of the data table is a position or a region, and/or a timing or time at which the target molecule is present. In this mode, an amount of the target molecules, and a space and/or time at which the target molecule is present is taken into consideration, whereby more appropriate labels are assigned to the target molecules. For example, in a case where the label is a dye, and also in this mode, a fluorescent dye that allows color separation to be performed more easily is assigned to the target molecule. This mode is suitable for, for example, observation of the target molecule using a fluorescence microscope, or analysis of the target molecule using various arrays.

In another preferred mode, the rule can be applied in such a case where the element of the data table is the data related to an amount of the target molecules, and one of the items of the data table is a species and/or a cell type in which the target molecule is present. In this mode, an amount of the target molecules, and an organism and/or a cell at which the target molecule is present is taken into consideration, whereby more appropriate labels are assigned to the target molecules. For example, in a case where the label is a fluorescent dye in this mode, an amount of the target molecules, and a species and/or a cell type at which the target molecule is present is taken into consideration, whereby more appropriate labels are assigned to the target molecules. Furthermore, in this mode, a fluorescent dye that allows color separation to be performed more easily is assigned to the target molecule. This mode is suitable for, for example, analysis of the target molecules based on flow cytometry.

(1-2) Second Exemplary Rule

A second example of the assignment rule is the following set of Rules 2 to 4.

Rule 2: A fluorescent dye for each of the target molecules is selected in such a manner that, with respect to two target molecules having positive correlation between data tables, a fluorescent dye having a farther wavelength is assigned to each of the target molecules having stronger correlation.

Rule 3: A fluorescent dye other than the fluorescent dye having already been assigned may be assigned to two target molecules having negative correlation between data tables. However, the fluorescent dye to be assigned according to Rule 3 is separated from the wavelength of the fluorescent dye having already been assigned by equal to or more than a predetermined wavelength.

Rule 4: Rule 2 is prioritized over Rule 3.

According to Rule 2, the label selection as descried in Rule 1 mentioned above can be carried out.

The fluorescent dye to be assigned according to Rule 3 is separated from the fluorescent dye having already been assigned by equal to or more than a predetermined wavelength, whereby the spectral overlap is reduced and the color separation can be performed more easily.

According to Rule 4, since Rule 2 is prioritized over Rule 3, the fluorescent dye is preferentially assigned to two target molecules having stronger positive correlation. As a result, more appropriate assignment can be carried out.

According to one mode of the present technology, assignment of labels to the target molecules having positive correlation can be prioritized over assignment of labels to the target molecules having negative correlation. In other words, the support information generator can preferentially assign labels to the two target molecules having positive correlation. This makes it possible to select a more appropriate label.

(1-3) Third Exemplary Rule

A third example of the assignment rule is the following set of Rules 5 to 7.

Rule 5: A predetermined wavelength region is divided by the number of target molecules having positive correlation between data tables, and one fluorescent dye selected from each of the divided wavelength range is assigned to each of the target molecules.

Rule 6: A fluorescent dye other than the fluorescent dye having already been assigned may be assigned to two target molecules having negative correlation between data tables. However, the fluorescent dye to be assigned according to Rule 6 is separated from the wavelength of the fluorescent dye having already been assigned by equal to or more than a predetermined wavelength.

Rule 7: Rule 5 is prioritized over Rule 6.

According to Rule 5, for example, a range of a wavelength region (e.g., 380 nm to 750 nm) of visible light is equally divided by the number of target molecules having positive correlation, and the fluorescent dyes belonging to respective divided wavelength ranges are assigned to the target molecules. Therefore, the spectral overlap is reduced, and the color separation can be easily performed.

According to Rule 6, the label selection as descried in Rule 3 mentioned above can be carried out. According to Rule 7, the fluorescent dye is preferentially assigned to the two target molecules having positive correlation, whereby more appropriate assignment can be carried out.

In Rule 5, in a case where a plurality of fluorescent dyes belongs to a certain wavelength range, it can be determined which fluorescent dye is to be selected among the plurality of fluorescent dyes in accordance with, for example, any of the following rules.

Rule 5-1: A fluorescent dye is selected such that the value expressed by (amount of target molecule)×(fluorescent intensity of fluorescent dye) is maximized.

Rule 5-2: A fluorescent dye is selected such that the value expressed by (amount of target molecule)×(fluorescent intensity of fluorescent dye) falls within a predetermined numerical range.

Rule 5-3: A fluorescent dye is selected such that the value expressed by (amount of target molecule)×(fluorescent intensity of fluorescent dye) falls within a predetermined numerical range, and the value is maximized or minimized in the range or the value is closest to the center of the range.

According to Rules 5-1 to 5-3 described above, labels can be appropriately narrowed down. According to Rules 5-1 to 5-3, for example, in a case where there is a plurality of label candidates, it is possible to select a smaller number of labels, for example, only one label.

For example, Rules 5-1 to 5-3 can be applied in a case where there is only one target molecule to be analyzed. Furthermore, Rules 5-1 to 5-3 may be applied in a case where, in Rule 3 described above, a fluorescent dye other than the fluorescent dye having already been assigned is to be assigned, or in a case where, in Rule 8 to be described below, one fluorescent dye is to be selected from a certain wavelength range.

Both of data related to an amount of the target molecules (e.g., expression level) and data related to fluorescent intensity of a fluorescent dye can be obtained from the database. Furthermore, the value of (expression level of target molecule)×(fluorescent intensity of fluorescent dye) itself may be obtained from the database. Those data can be obtained by the information processor.

(1-4) Fourth Exemplary Rule

A fourth example of the assignment rule is the following set of Rules 8 to 11.

Rule 8: A predetermined wavelength region is divided by the number of target molecules having positive correlation between data tables, and one fluorescent dye selected from each of the divided wavelength range is assigned to each of the target molecules.

Rule 9: In Rule 8, for two target molecules having stronger positive correlation, a fluorescent dye is selected from more distant wavelength ranges.

Rule 10: A fluorescent dye other than the fluorescent dye having already been assigned may be assigned to two target molecules having negative correlation between data tables. However, the fluorescent dye to be assigned according to Rule 2 is separated from the wavelength of the fluorescent dye having already been assigned by equal to or more than a predetermined wavelength.

Rule 11: Rule 8 is prioritized over Rule 10.

The selection of the fluorescent dye is performed according to Rules 8 and 9, whereby the spectral overlap is reduced, and the color separation can be performed more easily.

(1-5) Fifth Exemplary Rule

A fifth example of the assignment rule is the following Rule 12.

Rule 12: A predetermined wavelength region is divided by the number of target molecules having positive correlation between data tables, and a plurality of fluorescent dyes belonging to the respective divided wavelength ranges is presented as label candidates for the target molecule.

In accordance with Rule 12, the plurality of fluorescent dyes is presented to the user as label candidates, whereby the number of label options to be presented to the user can be increased, and the spectral overlap of the dyes to be selected can be reduced. For example, for two target molecules having negative correlation, the support information generator may optionally assign a label other than the already assigned label, or the user may make a selection as appropriate. Labels are assigned to the target molecules in accordance with the rules, whereby the spectral overlap is reduced and more appropriate labels can be assigned to the target molecules.

A rule for generating support information may be a combination of the rules described above. Furthermore, rules may be added by the user as appropriate, or the label selection support system according to the present technology may newly generate rules on the basis of machine learning.

A rule that does not need to refer to the data table can also be used as a rule for generating support information. Examples of such a rule include, but are not limited to, the following sixth and seventh exemplary rules.

(1-6) Sixth Exemplary Rule

A sixth example of the assignment rule is the following Rule 13.

Rule 13: A predetermined fluorescent dye is not presented as a label candidate for a certain target molecule.

Some fluorescent dyes should not be used as labels of target molecules for the reason that, for example, the fluorescent dyes adversely affect the physical properties of the target molecules. In such a case, Rule 13 can be applied.

(1-7) Seventh Exemplary Rule

A seventh example of the assignment rule is the following Rule 14.

Rule 14: A predetermined fluorescent dye is invariably selected for a certain target molecule.

In a case where there is a fluorescent dye that the user has already determined to use for the certain target molecule, Rule 14 can be applied. In a case where Rule 14 is applied, a fluorescent dye having a wavelength within a predetermined range from the fluorescence wavelength of the already determined fluorescent dye can be excluded from label candidates.

In the present technology, the support information generator generates the support information associated with assignment of a label in accordance with, for example, any of the rules or the set of rules described above, or in accordance with a rule group including the rules or the set of rules. Then, the generated support information is transmitted by the transmitter to, via the network, a terminal of the user who analyzes the target molecules, for example. The user refers to the support information to select a label used for the analysis.

(2) First Example of First Embodiment (Label Selection Support System)

Hereinafter, an exemplary label selection support system according to the present technology and label selection using the system will be described with reference to FIGS. 1 and 2.

FIG. 1 is a schematic diagram illustrating an exemplary situation in which the label selection support system according to the present technology is used. In FIG. 1, a label selection support system 100 is connected to a user terminal 102 and a database 103 via a network 101.

Figure 2:
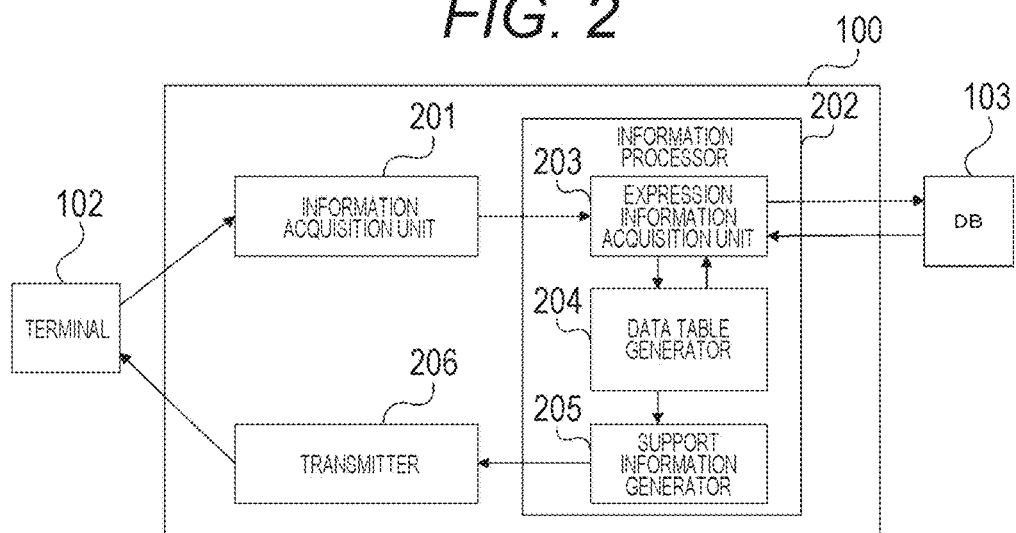
FIG. 2 is a block diagram illustrating an example of the label selection support system according to the present technology.

FIG. 2 is a block diagram of the label selection support system 100. The label selection support system 100 includes an information acquisition unit 201, an information processor 202, and a transmitter 206. The information processor 202 includes an expression information acquisition unit 203, a data table generator 204, and a support information generator 205. Note that the network 101 is omitted in FIG. 2.

The transmitter 206 of the label selection support system 100 transmits, via the network 101, data for causing the terminal 102 to display a screen prompting a user to input the name of a target molecule to be analyzed. The data may be stored in, for example, the information processor 202. In response to reception of the data, the terminal 102 displays the screen on a display unit of the terminal 102, such as a display. The screen may be provided with, for example, an input field for the name of the target molecule, and a transmission button for transmitting the input name to the label selection support system 100. In response to user input of the name of the target molecule and a click of the transmission button on the screen, the terminal 102 transmits the name of the target molecule to the label selection support system 100 via the network 101.

Furthermore, the screen may be provided with a field for inputting the name of a device used to analyze the target molecule. In response to input of the name of the device in addition to the name of the target molecule and a click of the transmission button, the terminal 102 transmits information associated with the name of the target molecule and the name of the device to the label selection support system 100.

The information acquisition unit 201 of the label selection support system 100 obtains the name of the target molecule via the network 101.

Furthermore, the information acquisition unit 201 may obtain the name of the device in addition to the name of the target molecule via the network 101.

The expression information acquisition unit 203 of the label selection support system 100 searches the database 103 using the name of the target molecule as a key. With the search being conducted, the expression information acquisition unit 203 obtains, from the database 103, data related to the name of the target molecule. The data includes, for example, the region where the target molecule is expressed in vivo and the expression level.

For example, the information processor 202 can select a database to be searched according to the name of the target molecule. Alternatively, the user who analyzes the target molecule may select the database to be searched in advance.

Furthermore, the information processor 202 can search the database 103 using the name of the device as a key. With the search being conducted, the information processor 202 can obtain, from the database 103, label data that can be used in the device.

The data table generator 204 of the label selection support system 100 generates, from the obtained data, a data table for each of the target molecules. The data table is, for example, a data table in which items of the cell type having been subject to the target molecule analysis and the expression region in the cell of the target molecule are included, and expression levels in various expression regions in each cell type is included in each cell. Examples of the data table are illustrated in FIGS. 4 and 5.

FIGS. 4 and 5 illustrate data used to generate a data table having expression levels in various expression regions in each cell type (A and B in each figure), and the data table generated by the data (C in each figure). Note that, in the present technology, a unit of the expression level may be selected by those skilled in the art as appropriate. It is ppm in FIGS. 4 and 5.

For example, the data table is generated as follows.

For example, the expression information acquisition unit 203 obtains, from a certain database, data of the expression level of a molecule 1 in cells A to F. The table A in the upper part of FIG. 4 illustrates expression levels in respective cell types. For example, as illustrated in FIG. 4A, a value of $1 \times 10^2$ is obtained as expression level data of the molecule 1 in the cell A. Furthermore, from the database or a database different from the database, data indicating a degree of expression in various cell regions of the cell A in five stages is obtained. The table B in the middle of FIG. 4 illustrates a degree of expression in each cell region. For example, the degree of expression of the molecule 1 in the plasma membrane of the cell A is five. Note that the degree of expression in the cells B to F is omitted in FIG. 4. The expression level data obtained as described above is multiplied by the expression degree data, thereby generating the data table illustrated in the lower part C of FIG. 4.

FIG. 5 illustrates expression level data and data indicating a degree of expression in various cell regions similarly obtained for a molecule 2, as well as a data table similarly generated.

The support information generator 205 of the label selection support system 100 refers to the generated data table to generate support information associated with assignment of a label.

A label to be assigned can be selected from, for example, the labels that can be used in the device obtained by the information processor 202. In a case where the device information cannot be used, for example, a label to be assigned is selected from a dye list stored in the information processor in advance. The dye list can be, for example, a list of commercially available fluorescent dyes having fluorescence wavelengths in the visible light region.

An example of support information generation will be described with reference to FIGS. 4 to 8.

FIGS. 4 and 5 are as described above.

The graphs related to the molecules 1 and 2 illustrated in FIG. 6 represent the respective data tables illustrated in FIGS. 4 and 5 in a three-dimensional matrix. The graphs related to molecules 3 and 4 in FIG. 6 represent, in a similar manner to the graphs related to the molecules 1 and 2, data tables generated for the molecules 3 and 4 in a three-dimensional matrix. The data tables for the molecules 3 and 4 are illustrated in FIG. 7 as described later. The data tables for the molecules 3 and 4 are also generated in a similar manner to the molecules 1 and 2.

For example, the support information generator 205 obtains a correlation coefficient between the data tables for the molecules 1 to 4, and then generates support information associated with label assignment for the molecules 1 to 4 on the basis of the correlation coefficient. The correlation coefficient is, for example, a cross-correlation coefficient, and a formula to be used to calculate the cross-correlation coefficient is, for example, as follows.

$$R_{NCCC} = \frac{\sum_{j=0}^{N-1} \sum_{i=0}^{M-1} (I(i,j) - \bar{I})(T(i,j) - \bar{T})}{\sqrt{\sum_{j=0}^{N-1} \sum_{i=0}^{M-1} (I(i,j) - \bar{I})^2 \times \sum_{j=0}^{N-1} \sum_{i=0}^{M-1} (T(i,j) - \bar{T})^2}} \quad \text{[Formula 1]}$$

In the formula above, M and N represent the number of rows and columns of the data table, T(i, j) represents data at the position (i, j) in one data table, and I(i, j) represents data at the position (i, j) in the other data table.

The cross-correlation coefficients between the respective molecules calculated according to the formula above are illustrated in FIG. 8. On the basis of the correlation coefficients illustrated in FIG. 8, support information associated with label assignment is generated according to, for example, the following rules 1 and 2.

Rule 1: Between molecules with positive correlation, dyes far in the fluorescence wavelength are assigned in descending order of the correlation coefficient.

Rule 2: Between molecules with negative correlation, dyes having close fluorescence wavelengths can be used.

Among the molecules 1 to 4, the combination of molecules having positive correlation between the molecules 1 and 2 and having the highest correlation coefficient is the combination of the molecules 1 and 2.

There is negative correlation between the molecules 1 and 3, molecules 1 and 4, molecules 2 and 3, molecules 2 and 4, and molecules 3 and 4.

In accordance with Rule 1, dyes far in the fluorescence wavelength are assigned to the molecules 1 and 2. In accordance with Rule 2, dyes having close fluorescence wavelengths can be used between the molecules 1 and 3, molecules 1 and 4, molecules 2 and 3, molecules 2 and 4, and molecules 3 and 4. Note that, in a case where the number of selectable dyes is small, a dye selected according to Rule 2 may be a dye having a wavelength same as that of the already selected dye.

In accordance with Rules 1 and 2, the support information generator 205 generates support information associated with dye assignment according to, for example, a mode to be described below.

In one mode, the support information generator 205 selects the molecules 1 and 2 as a combination of molecules having the highest correlation coefficient in accordance with Rule 1 mentioned above. Then, the support information generator 205 refers to a dye database (not illustrated) to assign, from a predetermined dye group, two dyes farthest in the fluorescence wavelength to the molecules 1 and 2. Then, the support information generator 205 generates support information indicating that the two dyes should be assigned to the molecules 1 and 2.

Next, the support information generator 205 generates support information indicating that dyes for the molecules 3 and 4 should be assigned from dyes other than the dyes having been assigned to the molecules 1 and 2.

In another mode, the support information generator 205 selects the molecules 1 and 2 as a combination of molecules having the highest correlation coefficient in accordance with Rule 1 mentioned above.

Here, the dyes included in the dye database to which the support information generator 205 refers are classified in advance into a group of dyes having wavelengths within a predetermined wavelength range. For example, wavelengths in the visible light region are divided into a plurality of ranges, such as 2 to 20, 3 to 15, and 4 to 10, and a plurality of dyes is classified into the plurality of ranges according to the fluorescence wavelengths of the dyes. More specific examples of the segmentation of the wavelength range can include 380 to 430 nm (purple), 430 to 490 nm (blue), 490 to 550 nm (green), 550 to 590 nm (yellow), 590 to 640 nm (orange), and 640 to 770 nm (red). A plurality of dyes may be classified in advance according to the fluorescence wavelength in each of the wavelength ranges divided in this manner, and a plurality of dye groups may be formed.

The support information generator 205 generates support information indicating that dyes should be selected for the molecules 1 and 2 from each of two dye groups farthest in the wavelength range (e.g., purple group and red group). Alternatively, the support information generator 205 may generate, as support information, a combination of dyes obtained by selecting one of the dyes belonging to each of the two dye groups farthest in the wavelength range.

Next, the support information generator 205 generate support information indicating that dyes should be assigned to the molecules 3 and 4 from the dyes belonging to dye groups other than the two dye groups described above presented to be selected for the molecules 1 and 2.

As described above, the support information generator 205 generates the support information associated with label assignment.

The transmitter 206 of the label selection support system 100 transmits the generated support information to the terminal 102 via the network. The terminal 102 displays the support information on, for example, a display. As a result, the user can refer to the support information to select a label suitable for the analysis of the target molecule.

(3) Second Example of First Embodiment (Label Selection Support System)

In one mode of the present technology, the information processor can further obtain data related to treatment conditions before analysis of biomolecules in addition to the expression information. In that case, the data table generator can generate, for each biomolecule, a treatment condition data table including the treatment conditions before analysis of biomolecules as items. The information processor can include a treatment condition selection unit that refers to the treatment condition data table generated for each biomolecule to select a treatment condition under which more biomolecules can be analyzed.

With the treatment condition selection unit being included, it becomes possible to present, to the user, more appropriate treatment conditions for a plurality of molecules. As a result, the user can select treatment conditions more easily.

Hereinafter, an exemplary case where the information processor further includes the treatment condition selection unit will be described with reference to FIGS. 1 and 9.

FIG. 1 is the same as that described above in "(2) First Example of First Embodiment (Label Selection Support System)".

Figure 9:
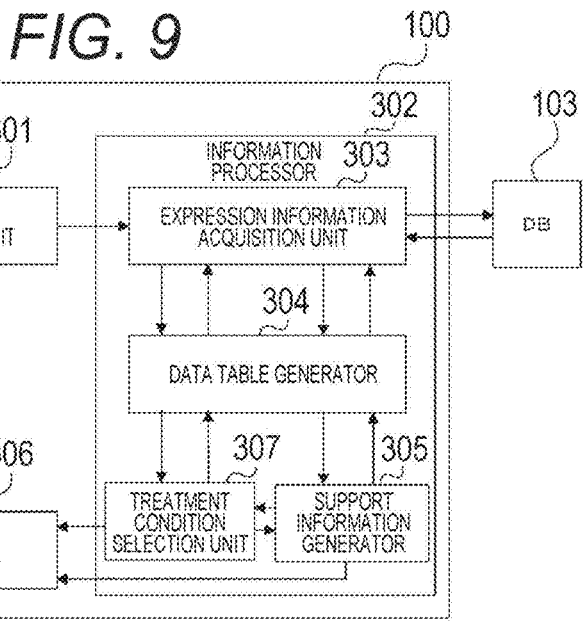
FIG. 9 is another block diagram illustrating an example of the label selection support system according to the present technology.

FIG. 9 illustrates a state in which a treatment condition selection unit 307 is added to the label selection support system 100 in FIG. 2 described above in "(2) First Example of First Embodiment (Label Selection Support System)".

The label selection support system 100 causes, via the network 101, the terminal 102 to display a screen prompting the user to input the name of a target molecule to be analyzed. The screen may be provided with, for example, an input field for the name of the target molecule, and a transmission button for transmitting the input name to the label selection support system 100. In response to user input of the name of the target molecule and a click of the transmission button on the screen, the terminal 102 transmits the name of the target molecule to the label selection support system 100 via the network 101.

The data for causing the terminal 102 to display the screen can be performed by, for example, a transmitter 306 of the label selection support system 100. The data may be stored in, for example, an information processor 302.

An information acquisition unit 301 of the label selection support system 100 obtains the name of the target molecule via the network 101.

An expression information acquisition unit 303 of the label selection support system 100 searches the database 103 using the name of the target molecule as a key. With the search being conducted, the expression information acquisition unit 303 obtains data related to the name of the target molecule. The data includes, for example, the region where the target molecule is expressed in vivo and the expression level, and the conditions of the processing performed before the analysis of the target molecule.

A data table generator 304 of the label selection support system 100 generates, from the obtained data, a data table for each of the target molecules. The data table to be generated is a data table regarding the expression level and the expression region, and a data table regarding pretreatment conditions.

The data table regarding the expression level and the expression region is as illustrated in FIGS. 4, 5, and 7 described above in "(2) First Example of First Embodiment (Label Selection Support System)".

The data table regarding pretreatment conditions can include treatment conditions before analysis of biomolecules as items. Furthermore, the data table regarding pretreatment conditions can include, in each cell, data related to a result of the treatment.

Figure 10:
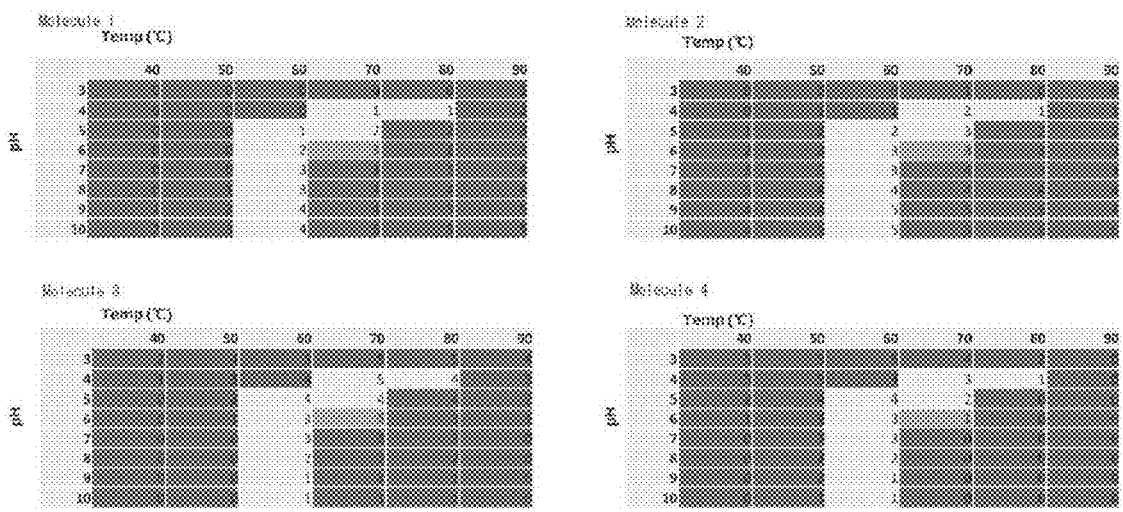
FIG. 10 is a data table regarding pretreatment conditions.

An example of the data table regarding pretreatment conditions is illustrated in FIG. 10. For example, as illustrated in FIG. 10, the data table regarding pretreatment conditions is created for each of the molecules 1 to 4 as follows.

For example, the expression information acquisition unit 303 obtains, from a certain database, pH and a temperature as pretreatment conditions for analysis of the molecule 1, and a degree of activation (particularly, activation of an antigen) based on the pretreatment. The degree of activation is expressed in six stages of 0 to 5, 0 indicates no activation, 1 indicates the lowest degree of activation, the degree of activation increases in the order from 1 to 5, and 5 indicates the highest degree of activation. A data table as illustrated in FIG. 10 is generated from the obtained data. Likewise, data tables as illustrated in FIG. 10 are generated for the molecules 2 to 4. The data table is a data table having pH and a temperature as items, and having a degree of activation in each cell.

The treatment condition selection unit 307 refers to the treatment condition data table created for each of the molecules 1 to 4 to select, among the molecules 1 to 4, a treatment condition under which more molecules can be analyzed.

For example, in FIG. 10, among the created data tables for the molecules 1 to 4, treatment conditions in the case where the degree of activation of all the molecules is equal to or more than 1 (i.e., activated case) are the case where the treatment conditions are 60° C. in temperature and pH 5 to 10, the case of 70° C. in temperature and pH 4 to 6, and the case of 80° C. in temperature and pH 4. Therefore, all of the molecules 1 to 4 are activated under those treatment conditions.

In one mode, the treatment condition selection unit 307 generates support information indicating that the pretreatment of the analysis of the molecules 1 to 4 should be performed under any of the conditions mentioned above in which all of the molecules 1 to 4 are activated.

In another mode, the treatment condition selection unit 307 can refer to the data table regarding the expression level and the expression region to select more appropriate pretreatment conditions. For example, as illustrated in FIG. 7, the molecule whose maximum expression level is the smallest is the molecule 1 ($5 \times 10^2$) among the molecules 1 to 4. In view of the above, among the pretreatment conditions under which all of the molecules 1 to 4 are activated, the pretreatment condition under which the degree of activation of the molecule 1 is maximized can be selected. In FIG. 10, in the case of 70° C. in temperature and pH 6, the degree of activation of the molecule 1 is 3 and that of other molecules is not more. Therefore, the treatment condition selection unit 307 generates support information indicating that the pretreatment of the analysis of the molecules 1 to 4 should be performed under the condition of 70° C. in temperature and pH 6.

In this mode, the treatment condition under which the molecule having a small expression level is more strongly activated is selected, whereby variations in fluorescent intensity detected in the fluorescent analysis for the molecules 1 to 4 can be suppressed in analysis after the treatment. For example, in flow cytometry using a plurality of fluorescent dyes, intensity of fluorescence emitted from the plurality of fluorescent dyes needs to be within a predetermined range. Therefore, this mode is particularly suitable for the selection of fluorescent dyes used for flow cytometry.

As described above in "(2) First Example of First Embodiment (Label Selection Support System)", the support information generator 305 generates the support information associated with assignment of a label.

In another mode, as described below, the support information generator 305 may refer to the treatment condition selected by the treatment condition selection unit 307 to generate support information associated with a label that should be assigned.

In other words, as described above, the treatment condition selection unit 307 selects the condition of 70° C. in temperature and pH6 as a pretreatment condition under which the degree of activation of the molecule 1 is maximized. In that case, the degrees of activation of the molecules 1 to 4 are, as illustrated in FIG. 10, 3, 3, 3, and 1, respectively. Furthermore, the maximum values of the expression levels of the molecules 1 to 4 are, as illustrated in FIG. 7, $5 \times 10^2$, $3 \times 10^3$, $5 \times 10^3$, and $1 \times 10^4$, respectively. In view of the above, for example, the support information generator 305 assigns a dye to the target molecule such that the difference in the value of (expression level)×(degree of activation)×(fluorescent intensity of dye) between molecules becomes smaller. Accordingly, dyes suitable for a batch analysis of the molecules 1 to 4 are selected. An example of the assignment will be described with reference to FIG. 11.

Figure 11:
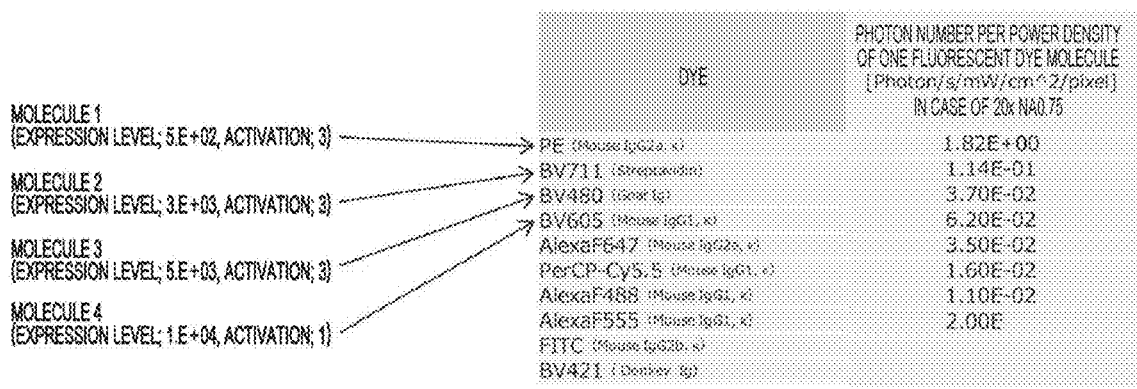
FIG. 11 is a table illustrating a manner of assigning dyes.

The table on the right side of FIG. 11 illustrates dyes and values of fluorescent intensity of the dyes. In the table, the dyes are arranged in descending order of fluorescent intensity from the top. On the left side of FIG. 11, the maximum expression levels and the degree of activation of the molecules 1 to 4 are indicated. In order to make the difference in the value of (expression level)×(degree of activation)×(fluorescent intensity of dye) between the molecules smaller, for example, PE is assigned to the molecule 1, BV711 is assigned to the molecule 2, BV480 is assigned to the molecule 3, and BV605 is assigned to the molecule 4. Regarding which dye should be assigned to make the difference in the value between the molecules described above smaller may be determined by known techniques in the art.

As described above, the support information generator 305 generates support information indicating that PE should be assigned to the molecule 1, BV711 should be assigned to the molecule 2, BV480 should be assigned to the molecule 3, and BV605 should be assigned to the molecule 4 to make the difference in the value of (expression level)×(degree of activation)×(fluorescent intensity of dye) between the molecules smaller.

The transmitter 306 of the label selection support system 100 transmits the support information associated with the pretreatment condition and the generated support information to the terminal 102 via the network. The terminal 102 displays those pieces of information. As a result, the user can refer to those pieces of information to select pretreatment conditions and labels suitable for the analysis of the molecules 1 to 4.

(4) Third Example of First Embodiment (Label Selection Support System)

In one mode of the present technology, the data table generator can further include a data table generation rule determiner that determines a generation rule of a data table using a classifier generated on the basis of information associated with target molecules and information associated with analysis of the target molecules.

Furthermore, in one mode of the present technology, the support information generator may further include a support information generation rule determiner that determines a generation rule of support information using a classifier generated on the basis of information associated with target molecules and information associated with analysis of the target molecules.

With the data table generation rule and/or the support information generation rule being determined as described above according to the present technology, it becomes possible to generate support information more appropriate for the analysis of the target molecules. Furthermore, learning data may increase in response to, for example, addition of new experimental data, addition of a new database itself to the database, or the like. In other words, information used for machine learning can be updated at any time. As a result, the data table generation rule and/or the support information generation rule is determined by the classifier in which the latest information is reflected, whereby more appropriate support information can be generated.

The classifier may have a data table generation rule and/or a support information generation rule set in advance, and/or may have a data table generation rule and/or a support information generation rule obtained by those generation rules being updated by machine learning using information in the database as learning data. Moreover, the classifier may have a data table generation rule and/or a support information generation rule newly obtained by machine learning using information in the database as learning data.

In the present technology, examples of the data table generation rule include, but are not limited to, rules regarding selection of a database from which data is obtained, selection of a type of data to be obtained, selection of an item of a data table to be generated, selection of the number of dimensions of a data table to be generated, and selection of a type of data in cells of a data table to be generated.

In the present technology, examples of the support information generation rule include, but are not limited to, the rules described above in "(1) Description of First Embodiment", "(2) First Example of First Embodiment (Label Selection Support System)", and "(3) Second Example of First Embodiment (Label Selection Support System)".

According to one mode of the present technology, the learning data used in the machine learning can include an analysis result obtained as a result of the analysis of the target molecules carried out by the user using the support information generated according to the present technology. In other words, feedback information from the user is used as a part of the learning data. As a result, it becomes possible to generate more appropriate support information.

Furthermore, according to one mode of the present technology, the learning data used in the machine learning may include user's evaluation on the support information generated according to the present technology. The evaluation of the user can be, for example, whether or not analysis has been carried out on the basis of the support information, whether or not the support information has served as a useful reference, whether or not the desired result has been obtained as a result of analysis based on the support information, or the like. With such user's evaluation being reflected to the classifier, it becomes possible to generate more appropriate support information.

Hereinafter, an exemplary case where the data table generator further includes the data table generation rule determiner and the support information generation rule determiner will be described with reference to FIGS. 1 and 12.

FIG. 1 is the same as that described above in "(2) First Example of First Embodiment (Label Selection Support System)".

Figure 12:
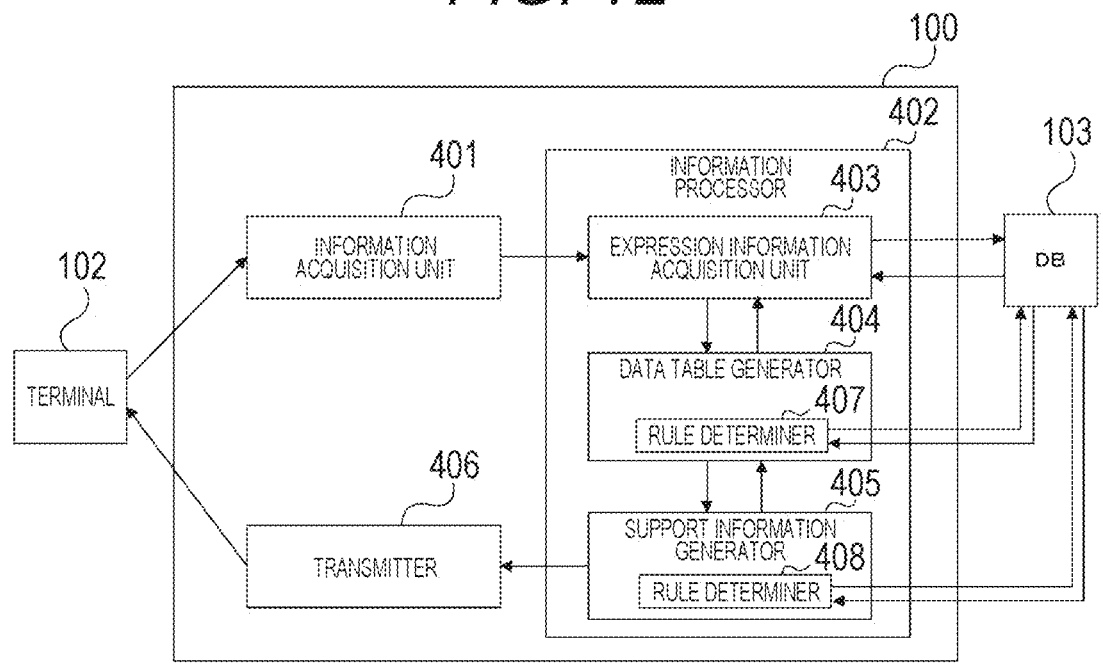
FIG. 12 is another block diagram illustrating an example of the label selection support system according to the present technology.

FIG. 12 illustrates a state in which a data table generation rule determiner 407 and a support information generation rule determiner 408 are added to the label selection support system 100 in FIG. 2 described above in "(2) First Example of First Embodiment (Label Selection Support System)". Although FIG. 12 illustrates a mode in which a data table generator 404 and a support information generator 405 include the data table generation rule determiner 407 and the support information generation rule determiner 408, respectively, the data table generation rule determiner 407 and the support information generation rule determiner 408 may be provided independently from the data table generator 404 and the support information generator 405.

In the same manner as the transmitter 206 described above in "(2) First Example of First Embodiment (Label Selection Support System)", a transmitter 406 of the label selection support system 100 transmits data for causing the terminal 102 to display a screen prompting the user to input the name of the target molecule to be analyzed via the network 101. Furthermore, in the same manner as the information acquisition unit 201, an information acquisition unit 401 of the label selection support system 100 obtains the name of the target molecule via the network 101. Furthermore, in the same manner as the expression information acquisition unit 203, an expression information acquisition unit 403 of the label selection support system 100 searches the database 103, and then the expression information acquisition unit 403 obtains data related to the name of the target molecule on the basis of the search.

The data table generator 404 of the label selection support system 100 generates, from the obtained data, a data table for each of the target molecules. The data table can be generated according to the data table generation rule determined by the data table generation rule determiner 407. The data table generation rule can be determined by a classifier generated on the basis of information associated with target molecules and information associated with analysis of the target molecules.

The classifier may have a data table generation rule set in advance, and/or a data table generation rule obtained by the data table generation rule being updated by machine learning using information in the database as learning data. Moreover, the classifier may have a data table generation rule newly obtained by machine learning using information in the database as learning data.

The data table generation rule can be, for example, rules regarding selection of a type of data in cells of the data table and/or selection of an item of the data table. Examples of the type of data in cells of the data table include the above-described expression level, the degree of expression, and the degree of activation. Examples of the item of the data table include a position or a region of expression, a cell type or a species, analytical conditions, a device or a reagent used in the analysis, treatment conditions before the analysis, and treatment conditions after the analysis.

The machine learning may be carried out according to methods known in the art. Examples of a machine learning method include logistic regression analysis, a support vector machine, and a neural network.

In the present technology, data to be used for the machine learning may be obtained from the database 103 by the data table generation rule determiner 407, or may be obtained from the database 103 by the expression information acquisition unit 403. The data obtained from the database 103 may include information associated with target molecules and information associated with analysis of the target molecules.

The information associated with target molecules is as described above in "(1) Description of First Embodiment".

The information associated with analysis of the target molecules is selected from, for example, "data related to analysis results of target molecules, analytical conditions, and an analyzer" described above in "(1) Description of First Embodiment".

The data table generator 404 generates the data table according to the data table generation rule determined by the data table generation rule determiner 407. Examples of the data table to be generated are as described above in "(1) Description of First Embodiment", "(2) First Example of First Embodiment (Label Selection Support System)", and "(3) Second Example of First Embodiment (Label Selection Support System)".

The support information generator 405 of the label selection support system 100 refers to the generated data table to generate support information associated with assignment of a label. The support information can be generated according to the support information generation rule determined by the support information generation rule determiner 408. The support information generation rule can be determined by a classifier generated on the basis of information associated with target molecules and information associated with analysis of the target molecules.

The classifier may have a support information generation rule set in advance, and/or a support information generation rule obtained by the support information generation rule being updated by machine learning using information in the database as learning data. Moreover, the classifier may have a support information generation rule newly obtained by machine learning using information in the database as learning data.

Examples of the support information generation rule include, but are not limited to, rules regarding how the data table is referenced, rules regarding from which target molecule assignment of a label is performed, rules regarding selection of a label to be assigned, rules regarding how a pretreatment condition is referenced, rules regarding how a correlation coefficient is calculated, and rules regarding how assignment of weights is performed.

The machine learning can be carried out according to methods known in the art. Examples of a machine learning method include logistic regression analysis, a support vector machine, and a neural network.

In the present technology, data to be used for the machine learning may be obtained from the database 103 by the support information generation rule determiner 408, or may be obtained from the database 103 by the expression information acquisition unit 403. The data obtained from the database 103 may include information associated with target molecules and information associated with analysis of the target molecules.

The information associated with target molecules is as described above in "(1) Description of First Embodiment".

The information associated with analysis of the target molecules can be, for example, "data related to analysis results of target molecules, analytical conditions, and an analyzer" described above in "(1) Description of First Embodiment".

The support information generator 405 generates support information according to the support information generation rule determined by the support information generation rule determiner 408. Examples of the support information to be generated are as described above in "(1) Description of First Embodiment", "(2) First Example of First Embodiment (Label Selection Support System)", and "(3) Second Example of First Embodiment (Label Selection Support System)".

The transmitter 406 of the label selection support system 100 transmits the generated support information to the terminal 102 via the network. The terminal 102 displays the support information on, for example, a display. As a result, the user can refer to the support information to select a label suitable for the analysis of the target molecule.

3. Second Embodiment (Label Selection Support Device)

(1) Description of Second Embodiment

The present technology provides a label selection support device including an information processor that obtains, using information associated with a plurality of target molecules to be analyzed, in vivo expression information of the plurality of target molecules from a database storing in vivo expression information of target molecules, and generates support information associated with assignment of a label to each of the plurality of target molecules on the basis of the expression information.

In the present technology, the support information associated with assignment of a label to each target molecule is generated as described above. By referring to the support information, a user can easily select a label suitable for analysis of each target molecule.

All of the items described in relation to the information processor in "2. First Embodiment (Label Selection Support System)" described above are applied to the label selection support device according to the present technology. For example, all of the items described in relation to the information acquisition unit, the expression information acquisition unit, the data table generator, the support information generator, and the treatment condition selection unit in "2. First Embodiment (Label Selection Support System)" described above are applied to the label selection support device according to the present technology. For example, the label selection support device according to the present technology may include an expression information acquisition unit, a data table generator, and a support information generator. The label selection support device according to the present technology may further include an information acquisition unit, a treatment condition selection unit, and/or a transmitter. Furthermore, each of the data table generator and the support information generator can include a data table generation rule determiner and a support information generation rule determiner as described above.

(2) Example of Second Embodiment (Label Selection Support Device)

Figure 13:
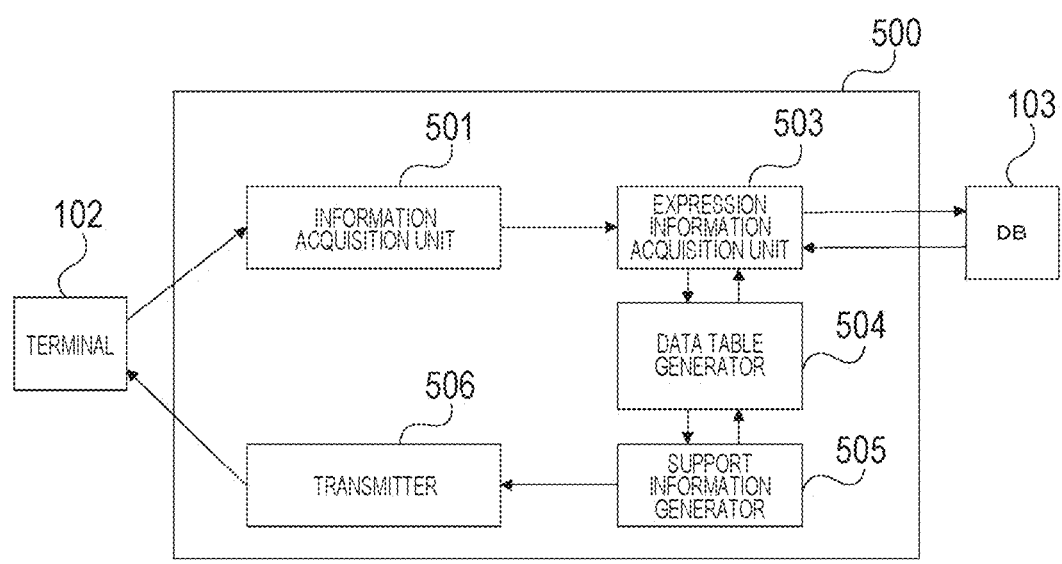
FIG. 13 is a block diagram illustrating an exemplary label selection support device according to the present technology.

An example of the label selection support device according to the present technology is illustrated in FIG. 13. FIG. 13 is a block diagram of a label selection support device 500. The label selection support device 500 includes an information acquisition unit 501, an expression information acquisition unit 503, a data table generator 504, a support information generator 505, and a transmitter 506. The information acquisition unit 501, the expression information acquisition unit 503, the data table generator 504, the support information generator 505, and the transmitter 506 are the same as the information acquisition unit 201, the expression information acquisition unit 203, the data table generator 204, the support information generator 205, and the transmitter 206 described in "(2) First Example of First Embodiment (Label Selection Support System)" of chapter 2. described above, respectively, and descriptions thereof will be omitted.

4. Third Embodiment (Method of Supporting Label Selection)

(1) Description of Third Embodiment

The present technology provides a method of supporting label selection including a step of, using information associated with a plurality of target molecules to be analyzed, obtaining expression information for obtaining in vivo expression information of the plurality of target molecules from a database storing in vivo expression information of target molecules, and a step of generating support information for generating support information associated with assignment of a label to each of the plurality of target molecules on the basis of the expression information.

In the present technology, support information that enables easy selection of a label suitable for analysis of the target molecules is generated by the method described above.

(2) First Example of Third Embodiment (Method of Supporting Label Selection)

Hereinafter, an example of the method of supporting label selection according to the present technology will be described with reference to FIGS. 1 and 14.

FIG. 1 is as described above in "2. First Embodiment (Label Selection Support System)".

Figure 14:
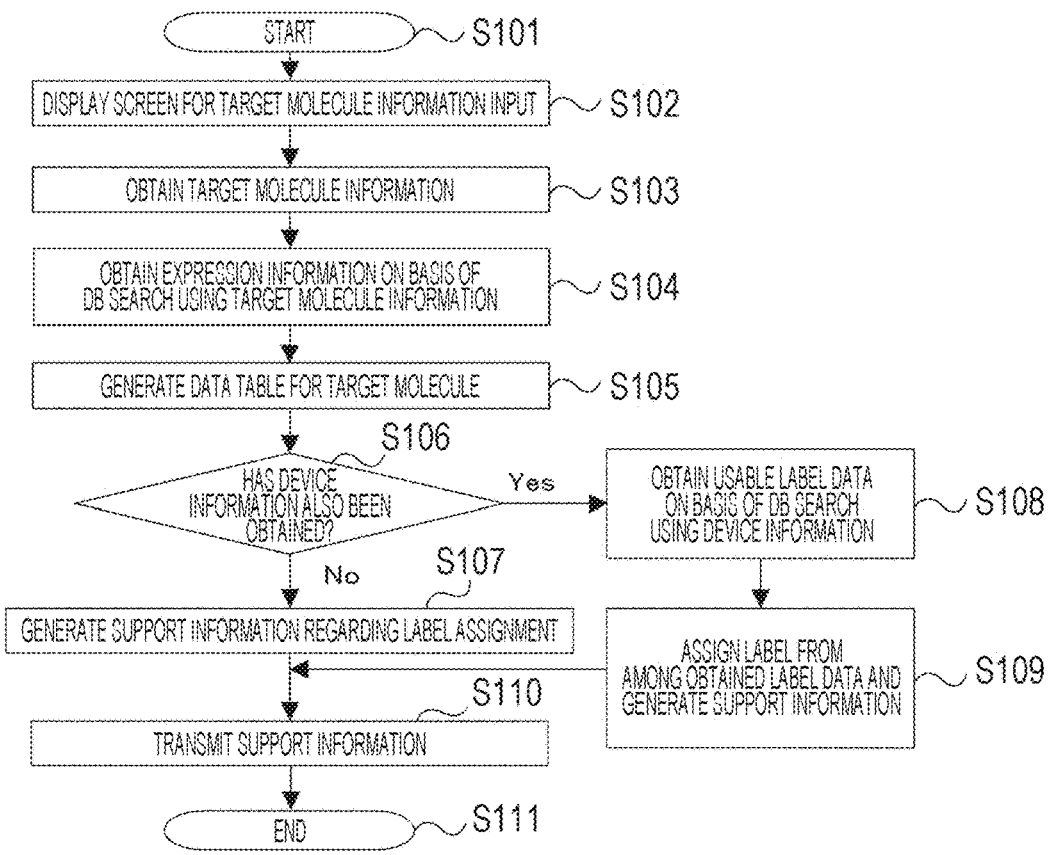
FIG. 14 is a flowchart illustrating an exemplary flow of a method of supporting label selection according to the present technology.

FIG. 14 is a flowchart illustrating an exemplary flow of the method of supporting label selection according to the present technology.

In step S101, a label selection support system 100 starts a process of label selection support according the present technology.

In step S102, the label selection support system 100 transmits, to a terminal 102, data for causing the terminal to display a screen prompting a user to input the name of a target molecule to be analyzed via a network 101. In response to reception of the data, the terminal 102 displays the screen on a display unit of the terminal 102, such as a display. In response to user input of the name of the target molecule and a click of the transmission button on the screen, the terminal 102 transmits the name of the target molecule to the label selection support system 100 via the network 101.

The screen may be provided with a field for inputting the name of a device used to analyze the target molecule. In response to input of the name of the device in addition to the name of the target molecule and a click of the transmission button, the terminal 102 transmits information associated with the name of the target molecule and the name of the device to the label selection support system 100.

In step S103, the label selection support system 100 obtains the name of the target molecule via the network 101. The label selection support system 100 may obtain the name of the device in addition to the name of the target molecule.

In step S104, the label selection support system 100 searches a database 103 using the name of the target molecule as a key to obtain data related to the name of the target molecule.

In step S105, the label selection support system 100 generates, from the obtained data, a data table for each of the target molecules. The generation of the data table can be performed by, for example, any of the methods described above in "2. First Embodiment (Label Selection Support System)". Furthermore, in step S105, as described in "(4) Third Example of First Embodiment (Label Selection Support System)" of chapter 2. described above, a generation rule of the data table can be determined before the generation of the data table.

In step S106, the label selection support system 100 determines whether or not the name of the device has been obtained in addition to the name of the target molecule in step S103. In response to the state that the name of the device has not been obtained, the label selection support system 100 proceeds with the process to step S107. In response to the state that the name of the device has been obtained, the label selection support system 100 proceeds with the process to step S108.

In step S107, the label selection support system 100 refers to the data table generated in step S105 to generate support information associated with assignment of a label. The generation of the support information can be performed by, for example, any of the methods described above in "2. First Embodiment (Label Selection Support System)". Furthermore, in step S107, as described in "(4) Third Example of First Embodiment (Label Selection Support System)" of chapter 2. described above, a generation rule of the support information can be determined before the generation of the support information.

In step S108, the label selection support system 100 obtains data of labels that can be used in the device.

In step S109, the label selection support system 100 generates support information associated with assignment of a label under the condition of selecting a label from the label data obtained in step S108. The generation of the support information can be performed by, for example, any of the methods described above in "2. First Embodiment (Label Selection Support System)". Furthermore, in step S109, as described in "(4) Third Example of First Embodiment (Label Selection Support System)" of chapter 2. described above, a generation rule of the support information can be determined before the generation of the support information.

In step S110, the label selection support system 100 transmits, to the terminal 102, the support information generated in step S107 or the support information generated in step S109 via the network 101.

In step S111, the label selection support system 100 terminates the process of label selection support according the present technology.

5. Fourth Embodiment (Program for Supporting Label Selection)

The present technology provides a program for supporting label selection that causes a computer to execute a step of, using information associated with a plurality of target molecules to be analyzed, obtaining expression information for obtaining in vivo expression information of the plurality of target molecules from a database storing in vivo expression information of target molecules, and a step of generating support information for generating support information associated with assignment of a label to each of the plurality of target molecules on the basis of the expression information.

In other words, the program for supporting label selection according to the present technology is a program for causing a computer to execute a method of supporting label selection according to the present technology. Each step to be executed by the program is as described above in "4. Third Embodiment (Method of Supporting Label Selection)", and descriptions thereof will be omitted.

6. Exemplary Hardware Configuration

Figure 15:
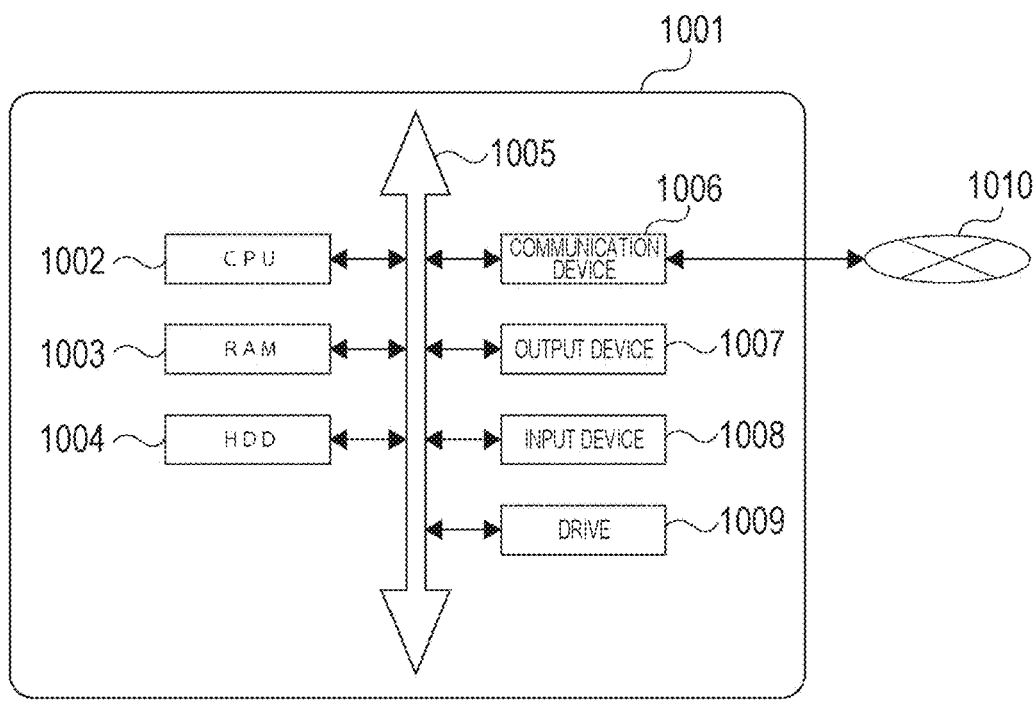
FIG. 15 is a diagram illustrating an exemplary schematic hardware configuration of an information processing apparatus that implements the label selection support system according to the present technology.

Hereinafter, an exemplary hardware configuration of an information processing apparatus that implements a label selection support system or a label selection support device according to the present technology will be described with reference to FIG. 15. FIG. 15 is a diagram illustrating an exemplary schematic hardware configuration of the information processing apparatus that implements the label selection support system according to the present technology.

An information processing apparatus 1001 illustrated in FIG. 15 includes a central processing unit (CPU) 1002, and a RAM 1003. The CPU 1002 and the RAM 1003 are mutually connected via a bus 1005, and are also connected to other components of the information processing apparatus 1001 via the bus 1005.

The CPU 1002 performs control and computing of the information processing apparatus 1001. Any processor can be used as the CPU 1002, and examples thereof include processors of a Xeon (registered trademark) series, a Core (trademark) series, and an Atom (trademark) series. Each component of the label selection support system 100 described with reference to FIG. 2 can be implemented by, for example, the CPU 1002.

The RAM 1003 includes, for example, a cache memory, and a main memory, and can temporarily store a program used by the CPU 1002 and the like.

The information processing apparatus 1001 may include a disk 1004, a communication device 1006, an output device 1007, an input device 1008, and a drive 1009. Any of those components can be connected to the bus 1005.

The disk 1004 can store an operating system (e.g., WINDOWS (registered trademark), UNIX (registered trademark), LINUX (registered trademark), etc.), a program for supporting label selection according to the present technology, other various programs, and various types of data.

The communication device 1006 connects the information processing apparatus 1001 to a network 1010 by wire or wirelessly. The communication device 1006 is a device that enables communication with a database and a terminal via the network 1010. A type of the communication device 1006 may be selected by those skilled in the part as appropriate.

The output device 1007 can output a processing result of the information processing apparatus 1001. Examples of the output device 1007 include, but are not limited to, a display device such as a display, an audio output device such as a speaker, and a printer.

The input device 1008 is a device for a user (e.g., administrator of the label selection support system) to operate the information processing apparatus 1001. Examples of the input device 1008 include, but are not limited to, a mouse and a keyboard.

The drive 1009 can read out information recorded in a recording medium and output it to the RAM 1003 and/or write various data in the recording medium. Examples of the recording medium include, but are not limited to, a DVD medium, a flash memory, and an SD memory card.

Note that the present technology can also employ the following configurations.

[1] A label selection support system including:
an information acquisition unit that obtains, via a network, information associated with a plurality of target molecules to be analyzed;
an information processor that obtains, by using the information associated with the plurality of target molecules, in vivo expression information of the plurality of target molecules from a database storing in vivo expression information of target molecules, and generates support information associated with assignment of a label to each of the plurality of target molecules on the basis of the expression information; and
a transmitter that transmits the generated support information via the network.

[2] The label selection support system according to [1], in which the expression information is information associated with in vivo expression distribution and/or an in vivo expression level.

[3] The label selection support system according to [1], in which the expression information is information associated with an in vivo expression level, and the information processor selects fluorescent intensity of a label to be assigned to the target molecules on the basis of the information associated with the expression level of the target molecules.

[4] The label selection support system according to [1], in which the expression information is information associated with in vivo expression distribution, and the information processor selects a fluorescence wavelength of a label to be assigned to the target molecules on the basis of the information associated with the expression distribution of the target molecules.

[5] The label selection support system according to any one of [1] to [4], in which the information processor assigns a fluorescent dye far in fluorescence wavelength spectrum to each of the plurality of target molecules spatially adjacent to each other.

[6] The label selection support system according to any one of [1] to [5], in which the information processor uses a learned model in which suitability of a combination of a target molecule and a label has been learned to generate the support information.

[7] The label selection support system according to any one of [1] to [6], in which the information processor includes a data table generator that generates a data table for each of the target molecules from the expression information.

[8] The label selection support system according to [7], in which the information processor further includes a support information generator that refers to the generated data table and generates support information associated with a label to be assigned to each of the target molecules.

[9] The label selection support system according to [8], in which the support information generator generates the support information on the basis of a correlation between the generated data tables.

[10] The label selection support system according to any one of [1] to [9], in which the label is a dye.

[11] The label selection support system according to any one of [8] to [10], in which
the label is a fluorescent dye, and
the support information generator assigns a label to each of the target molecules in such a manner that, on the basis of a correlation between the generated data tables, a fluorescent dye farther in wavelength is assigned to each of two target molecules having a stronger correlation between the data tables.

[12] The label selection support system according to any one of [7] to [11], in which the data table generator further includes a data table generation rule determiner that determines a generation rule of the data table using a classifier generated on the basis of information associated with target molecules and information associated with analysis of the target molecules.

[13] The label selection support system according to any one of [8] to [12], in which the support information generator further includes a support information generation rule determiner that determines a generation rule of the support information using a classifier generated on the basis of information associated with target molecules and information associated with analysis of the target molecules.

[14] The label selection support system according to any one of [1] to [13], in which the target molecules are biomolecules.

[15] The label selection support system according to any one of [7] to [14], in which the data table generator generates, for each of the target molecules, a data table having data related to an amount of the target molecules in a cell.

[16] The label selection support system according to any one of [1] to [15], in which the information processor also obtains, in addition to the expression information, data related to a treatment condition before analysis of a biomolecule.

[17] The label selection support system according to any one of [7] to [16], in which the data table generator generates, for each biomolecule, a treatment condition data table including a treatment condition before analysis of the biomolecule as an item.

[18] The label selection support system according to [17], in which the information processor further includes a treatment condition selection unit that refers to the treatment condition data table generated for each biomolecule to select a treatment condition under which more biomolecules can be analyzed.

[19] The label selection support system according to any one of [1] to [18], in which
the information processor is further configured to:
obtain device information associated with a device for analyzing the target molecules;
obtain, from a database, label data that can be used in the device on the basis of the device information; and
select a label to be assigned to the target molecules from labels included in the label data.

[20] A label selection support device including an information processor that obtains, by using information associated with a plurality of target molecules to be analyzed, in vivo expression information of the plurality of target molecules from a database storing in vivo expression information of target molecules, and generates support information associated with assignment of a label to each of the plurality of target molecules on the basis of the expression information.

[21] A method of supporting label selection, including:
an expression information obtaining step of, by using information associated with a plurality of target molecules to be analyzed, obtaining in vivo expression information of the plurality of target molecules from a database storing in vivo expression information of the target molecules; and
a support information generating step of generating support information associated with assignment of a label to each of the plurality of target molecules on the basis of the expression information.

[22] A program for supporting label selection, causing a computer to execute:
an expression information obtaining step of, by using information associated with a plurality of target molecules to be analyzed, obtaining in vivo expression information of the plurality of target molecules from a database storing in vivo expression information of the target molecules; and
a support information generating step of generating support information associated with assignment of a label to each of the plurality of target molecules on the basis of the expression information.

REFERENCE SIGNS LIST

100 Label selection support system
101 Network
102 Terminal
201 Information acquisition unit
202 Information processor
203 Expression information acquisition unit
204 Data table generator
205 Support information generator
206 Transmitter

The invention claimed is:

1. A label selection support system comprising:
circuitry configured to function as an information acquisition unit that obtains, via a network, information associated with a plurality of target molecules to be analyzed;
an information processor that obtains, by using the information associated with the plurality of target molecules, in vivo expression information of the plurality of target molecules from a database storing in vivo expression information of target molecules, and generates support information associated with assignment of a label to each of the plurality of target molecules on a basis of the expression information; and
a transmitter that transmits the generated support information via the network.

2. The label selection support system according to claim 1, wherein the expression information is information associated with in vivo expression distribution or an in vivo expression level.

3. The label selection support system according to claim 1, wherein the expression information is information associated with an in vivo expression level, and the information processor selects fluorescent intensity of a label to be assigned to the target molecules on a basis of the information associated with the expression level of the target molecules.

4. The label selection support system according to claim 1, wherein the expression information is information associated with in vivo expression distribution, and the information processor selects a fluorescence wavelength of a label to be assigned to the target molecules on a basis of the information associated with the expression distribution of the target molecules.

5. The label selection support system according to claim 1, wherein the information processor assigns a fluorescent dye far in fluorescence wavelength spectrum to each of the plurality of target molecules spatially adjacent to each other.

6. The label selection support system according to claim 1, wherein the information processor uses a learned model in which suitability of a combination of a target molecule and a label has been learned to generate the support information.

7. The label selection support system according to claim 1, wherein the information processor includes a data table generator that generates a data table for each of the target molecules from the expression information.

8. The label selection support system according to claim 7, wherein the information processor further includes a support information generator that refers to the generated data table and generates support information associated with a label to be assigned to each of the target molecules.

9. The label selection support system according to claim 8, wherein the support information generator generates the support information on a basis of a correlation between the generated data tables.

10. The label selection support system according to claim 8, wherein
the label is a fluorescent dye, and
the support information generator assigns a label to each of the target molecules in such a manner that, on a basis of a correlation between the generated data tables, a fluorescent dye farther in wavelength is assigned to each of two target molecules having a stronger correlation between the data tables.

11. The label selection support system according to claim 8, wherein the support information generator further includes a support information generation rule determiner that determines a generation rule of the support information using a classifier generated on a basis of information associated with target molecules and information associated with analysis of the target molecules.

12. The label selection support system according to claim 7, wherein the data table generator further includes a data table generation rule determiner that determines a generation rule of the data table using a classifier generated on a basis of information associated with target molecules and information associated with analysis of the target molecules.

13. The label selection support system according to claim 7, wherein the data table generator generates, for each of the target molecules, a data table having data related to an amount of the target molecules in a cell.

14. The label selection support system according to claim 7, wherein the data table generator generates, for each biomolecule, a treatment condition data table including a treatment condition before analysis of the biomolecule as an item.

15. The label selection support system according to claim 14, wherein the information processor further includes a treatment condition selection unit that refers to the treatment condition data table generated for each biomolecule to select a treatment condition under which more biomolecules can be analyzed.

16. The label selection support system according to claim 1, wherein the label is a dye.

17. The label selection support system according to claim 1, wherein the target molecules are biomolecules.

18. The label selection support system according to claim 1, wherein the information processor also obtains, in addition to the expression information, data related to a treatment condition before analysis of a biomolecule.

19. The label selection support system according to claim 1, wherein
the information processor is further configured to:
obtain device information associated with a device for analyzing the target molecules;
obtain, from a database, label data that can be used in the device on a basis of the device information; and
select a label to be assigned to the target molecules from labels included in the label data.

20. A label selection support device comprising:
an information processor that
obtains, by using information associated with a plurality of target molecules to be analyzed, in vivo expression information of the plurality of target molecules from a database storing in vivo expression information of target molecules, and
generates support information associated with assignment of a label to each of the plurality of target molecules on a basis of the expression information.

21. A method of supporting label selection, comprising:
by using information associated with a plurality of target molecules to be analyzed, obtaining in vivo expression information of the plurality of target molecules from a database storing in vivo expression information of the target molecules; and
generating support information associated with assignment of a label to each of the plurality of target molecules on a basis of the expression information.

22. A non-transitory storage medium encoded with instructions that, when executed by a computer, execute a method comprising:
by using information associated with a plurality of target molecules to be analyzed, obtaining in vivo expression information of the plurality of target molecules from a database storing in vivo expression information of the target molecules; and
generating support information associated with assignment of a label to each of the plurality of target molecules on a basis of the expression information.

* * * * *